(12) United States Patent
Griffiths et al.

(10) Patent No.: US 10,130,436 B2
(45) Date of Patent: Nov. 20, 2018

(54) AUTOMATED STRUCTURE WITH PRE-ESTABLISHED ARM POSITIONS IN A TELEOPERATED MEDICAL SYSTEM

(71) Applicant: INTUITIVE SURGICAL OPERATIONS, INC., Sunnyvale, CA (US)

(72) Inventors: Paul G Griffiths, Santa Clara, CA (US); Brandon D Itkowitz, Sunnyvale, CA (US); Thomas R Nixon, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 165 days.

(21) Appl. No.: 15/125,683

(22) PCT Filed: Mar. 17, 2015

(86) PCT No.: PCT/US2015/021108
§ 371 (c)(1),
(2) Date: Sep. 13, 2016

(87) PCT Pub. No.: WO2015/142955
PCT Pub. Date: Sep. 24, 2015

(65) Prior Publication Data
US 2017/0000575 A1    Jan. 5, 2017

Related U.S. Application Data

(60) Provisional application No. 61/954,083, filed on Mar. 17, 2014.

(51) Int. Cl.
*B25J 9/06*        (2006.01)
*A61B 34/35*      (2016.01)
(Continued)

(52) U.S. Cl.
CPC .............. *A61B 34/35* (2016.02); *A61B 34/25* (2016.02); *A61B 34/30* (2016.02); *A61B 46/10* (2016.02);
(Continued)

(58) Field of Classification Search
CPC ......... A61B 34/30; A61B 34/25; A61B 34/35; A61B 46/10; A61B 2017/00017;
(Continued)

(56) References Cited

U.S. PATENT DOCUMENTS 4,221,997 A * 9/1980 Flemming ................ B25J 9/046
                                                                  318/568.13
6,546,277 B1   4/2003 Franck, I et al.
(Continued)

FOREIGN PATENT DOCUMENTS

WO    WO-03077101 A2    9/2003

OTHER PUBLICATIONS

Extended European Search Report for Application No. 15764549.0, dated Oct. 20, 2017, 7 pages.
(Continued)

*Primary Examiner* — Dalena Tran

(57) ABSTRACT

A teleoperational medical system for performing a medical procedure in a surgical field includes a teleoperational assembly having a plurlity of motorized surgical arms configured to assist in a surgical procedure. It also includes an input device configured to receive an input to move all the arms of the plurality of motorized surgical arms to a pre-established position. A processing system is configured to receive the input form the input device and output control signals to each arm of the plurality of motorized surgical arms to move each arm to the pre-established position.

23 Claims, 22 Drawing Sheets

(51) Int. Cl.
- *A61B 34/00* (2016.01)
- *A61B 34/30* (2016.01)
- *A61B 50/10* (2016.01)
- *A61B 50/13* (2016.01)
- *A61B 46/10* (2016.01)
- *A61B 50/18* (2016.01)

(52) U.S. Cl.
CPC .............. *A61B 50/10* (2016.02); *A61B 50/13* (2016.02); *A61B 2050/105* (2016.02); *A61B 2050/185* (2016.02)

(58) Field of Classification Search
CPC . A61B 34/70; B25J 13/088; B25J 9/06; B25J 9/1682; B25J 9/1689; B25J 9/1694; G05D 1/0011; Y10S 901/02
USPC ..... 700/245; 606/1, 108, 130; 600/104, 114, 600/118; 128/898
See application file for complete search history.

(56) References Cited

U.S. PATENT DOCUMENTS

| | | |
|---|---|---|
| 6,963,792 B1 | 11/2005 | Green |
| 7,259,906 B1* | 8/2007 | Islam ..................... H01S 3/302 |
| | | 359/327 |
| 2004/0034282 A1 | 2/2004 | Quaid, III |
| 2011/0071543 A1 | 3/2011 | Prisco et al. |
| 2013/0303891 A1 | 11/2013 | Chopra |
| 2013/0325031 A1 | 12/2013 | Schena et al. |
| 2013/0325033 A1 | 12/2013 | Schena et al. |

OTHER PUBLICATIONS

International Search Report and Written Opinion for Application No. PCT/US15/21108, dated Jun. 8, 2015, 14 pages.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

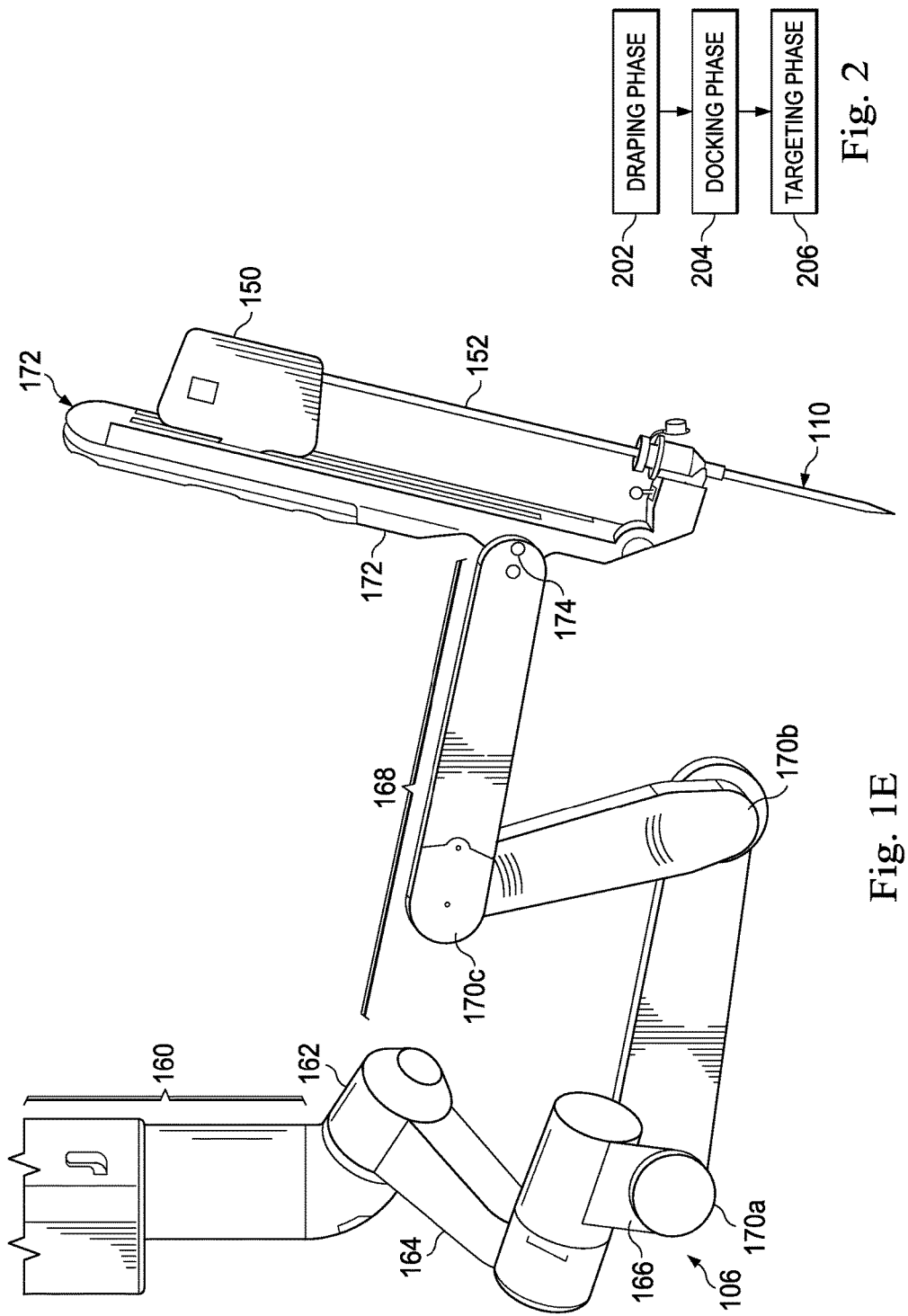

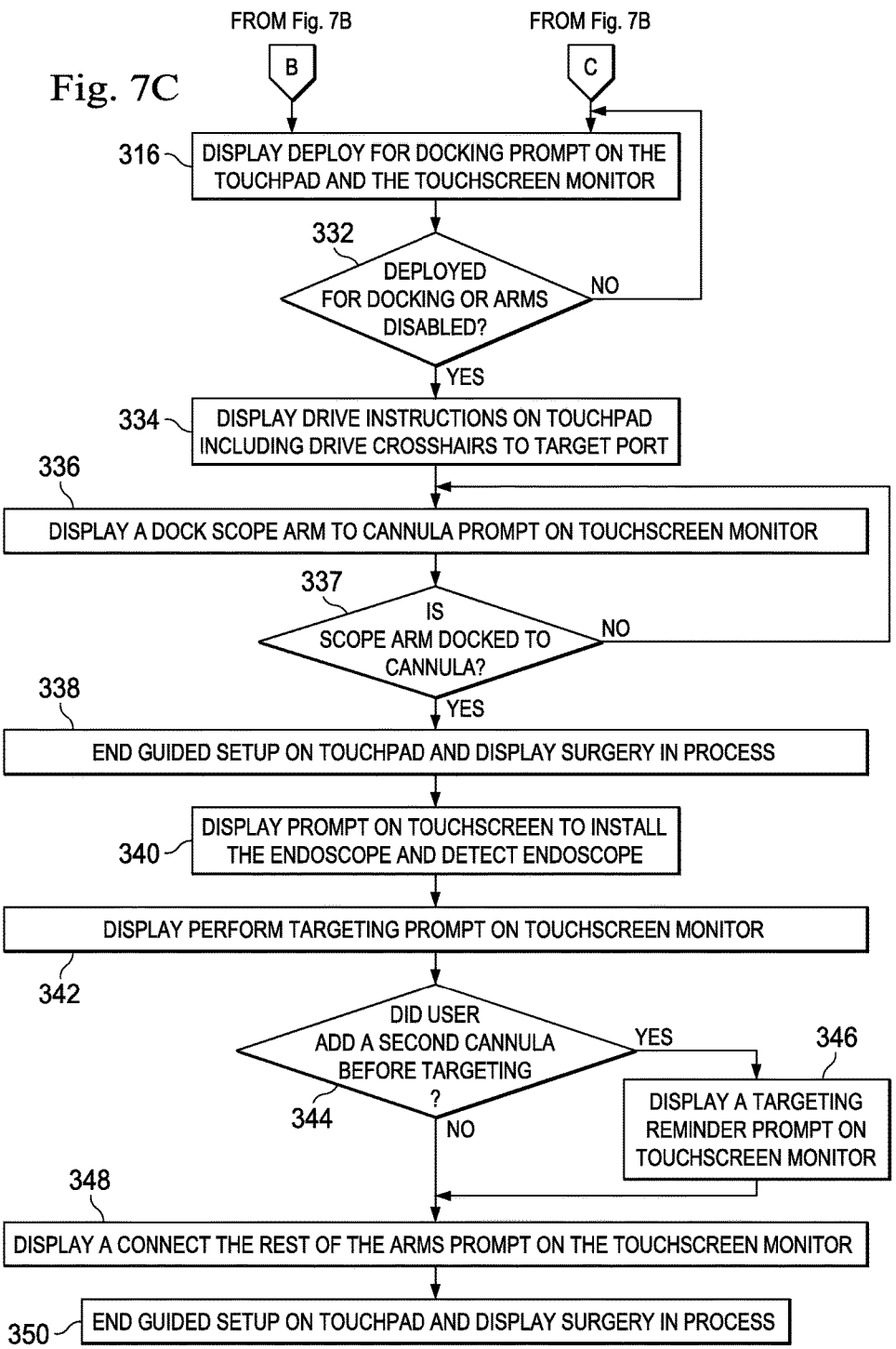

AUTOMATED STRUCTURE WITH PRE-ESTABLISHED ARM POSITIONS IN A TELEOPERATED MEDICAL SYSTEM

PRIORITY

This patent application is the U.S. national phase of International Application No. PCT/US2015/021108, filed Mar. 17, 2015, which claims priority to and the benefit of the filing date of U.S. Provisional Patent Application 61/954,083, titled "Automated Structure With Pre-Established Arm Positions in a Teleoperated Medical System," filed Mar. 17, 2014, which are incorporated herein by reference in their entirety.

FIELD

The present disclosure is directed to systems and methods for controlling an imaging instrument and more particularly to systems and methods for an automated setup with pre-established arm positions in a teleoperated medical system.

BACKGROUND

Surgical procedures can be performed using a teleoperational medical system in a minimally invasive manner. The benefits of a minimally invasive surgery are well known and include less patient trauma, less blood loss, and faster recovery times when compared to traditional, open incision surgery. In addition, the use of a teleoperational medical system, such as the DA VINCI® Surgical System commercialized by Intuitive Surgical, Inc., Sunnyvale, Calif., is known. Such teleoperational medical systems may allow a surgeon to operate with intuitive control and increased precision when compared to manual minimally invasive surgeries.

A teleoperational medical system may include one or more instruments that are coupled to one or more robotic arms. If the system is used to perform minimally invasive surgery, the instruments may access the surgical area through one or more small openings in the patient, such as small incisions or natural orifices, such as, for example, the mouth, urethra, or anus. In some cases, rather than having the instrument(s) directly inserted through the opening(s), a cannula or other guide element can be inserted into each opening and the instrument can be inserted through the cannula to access the surgical area. An imaging tool such as an endoscope can be used to view the surgical area, and the image captured by the imaging tool can be displayed on an image display to be viewed by the surgeon during a surgery.

It is desirable to provide teleoperational medical systems that can be effectively controlled in a manner that eases use, repeatability, and operation of a complex teleoperated medical system during setup and during minimally invasive medical procedures. The systems and methods disclosed herein overcome one or more of the deficiencies of the prior art.

SUMMARY

In an exemplary aspect, the present disclosure is directed to a teleoperational medical system for performing a medical procedure in a surgical field. The system includes a teleoperational assembly having a motorized setup structure and a plurality of motorized surgical arms configured to assist in a surgical procedure. An input device is configured to receive an input to move all the arms of the plurality of motorized surgical arms to a pre-established position. A processing system is configured to receive the input from the input device and output control signals to the setup structure and each arm of the plurality of motorized surgical arms to move the setup structure and each arm to the pre-established position.

In an aspect, the input device is configured to receive an input identifying a portion of a patient's anatomy to be treated in the surgical procedure, the pre-established position being based on the input identifying a portion of the patient's anatomy. In an aspect, the input device is configured to receive an input identifying an approach to the patient to be treated in the surgical procedure, the pre-established position being based on the input identifying the patient approach. In an aspect, the approach to the patient to be treated is one of a left side, a right side, and a leg approach. In an aspect, the pre-established position is a docking position wherein the setup structure and each arm of the plurality of motorized surgical arms is deployed in a position for advancing over a patient on a surgical bed. In an aspect, the teleoperational assembly comprises a boom and a rotatable platform rotatably connected to the boom, the motorized surgical arms extending from the rotatable platform, the processing system configured to rotate the rotatable platform relative to the boom in response to the input received at the input device. In an aspect, the plurality of motorized surgical arms each have a total range of motion and the pre-established docking position for each surgical arm is within a range of 30-70% of the total range of motion. In an aspect, the teleoperational assembly comprises a telescoping column and a telescoping boom extending from the column, the plurality of motorized surgical arms being carried on the boom, wherein the boom has a total range of motion, and the pre-established docking position for the boom is within a range of 30-70% of the total range of motion. In an aspect, the pre-established position is a draping position wherein each arm of the plurality of motorized surgical arms is deployed in a position suitable for receiving surgical drapes. In an aspect, the teleoperational assembly comprises a column with an adjustable height, and a boom extending from the column. The has an adjustable length, and the plurality of motorized surgical arms are carried on the boom. The draping position comprises a partially raised column and a partially extended boom. In an aspect, the pre-established position is a stow position wherein each arm of the plurality of motorized surgical arms is deployed in a fully retracted position to minimize the overall footprint of the teleoperational assembly. In an aspect, the teleoperational assembly comprises: a column with an adjustable height; and a boom extending from the column. The boom has an adjustable length and the plurality of motorized surgical arms are carried on the boom. The stowed position comprises a fully retracted column and fully retracted surgical arms.

In an exemplary aspect, the present disclosure is directed to a method of controlling arms of a teleoperational medical system. The method includes receiving an input at a user interface to move all arms of a plurality of motorized surgical arms of a teleoperational assembly to a pre-established position; and outputting a control signal to each arm of the plurality of motorized surgical arms to move each arm of the plurality of motorized surgical arms to the pre-established position.

In an aspect, the method includes receiving an input identifying a portion of a patient's anatomy to be treated in the surgical procedure, and wherein the control signal to each arm is based on the input identifying a portion of the patient's anatomy. In an aspect, the method includes receiving an input identifying an approach to the patient to be treated in the surgical procedure, and wherein the control signal to each arm is based on the input identifying the patient approach. In an aspect, receiving an input identifying an approach comprises receiving one of a left side approach, a right side approach, and a leg approach. In an aspect, outputting a control signal to each arm comprises outputting a control signal to raise each arm of the plurality of motorized surgical arms to a position for advancing over a patient on a surgical bed. In an aspect, the teleoperational assembly comprises a boom and an platform portion rotatably connected to the boom, the motorized surgical arms extending from the platform portion, further comprising outputting a control signal to the platform portion to rotate the platform portion relative to the boom in response to the input received at the input device. In an aspect, the plurality of motorized surgical arms each have a total range of motion and the pre-established position for each surgical arm is within a range of 30-70% of the total range of motion.

In an exemplary aspect, the present disclosure is directed to a method of controlling arms of a teleoperational medical system. The method includes receiving an anatomical input identifying a portion of a patient's anatomy to be treated in a surgical procedure; receiving an approach input identifying an approach to the patient to be treated in the surgical procedure; and outputting a control signal to each arm of a plurality of motorized surgical arms of a teleoperational assembly to move each arm of the plurality of motorized surgical arms to a pre-established position based on both the anatomical input identifying a portion of the patient's anatomy and the approach input identifying the approach to the patient.

In an aspect, the method includes receiving an actuating input at a user interface to move all arms of a plurality of motorized surgical arms of a teleoperational assembly to the pre-established position, wherein outputting a control to each arm is in response to the actuating input. In an aspect, outputting the control to each arm occurs only while the actuating input is being received.

These and other embodiments are further discussed below with respect to the following figures.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 1B illustrates a front elevation view of an exemplary teleoperational assembly according to one embodiment of the present disclosure. FIG. 1C illustrates a front elevation view of an exemplary operator input system according to one embodiment of the present disclosure. FIG. 1D illustrates a front view of an exemplary vision cart component according to one embodiment of the present disclosure.

FIG. 1E illustrates an arm of the exemplary teleoperational assembly of FIG. 1B according to one embodiment of the present disclosure.

FIG. 2 illustrates an exemplary flow chart showing phases of a guided setup system disclosed herein according to one embodiment of the present disclosure.

FIGS. 7A, 7B, and 7C are flow charts that illustrate an exemplary method of setting the teleoperational medical system using the guided setup system according to one embodiment of the present disclosure.

DETAILED DESCRIPTION

Figure 1A:
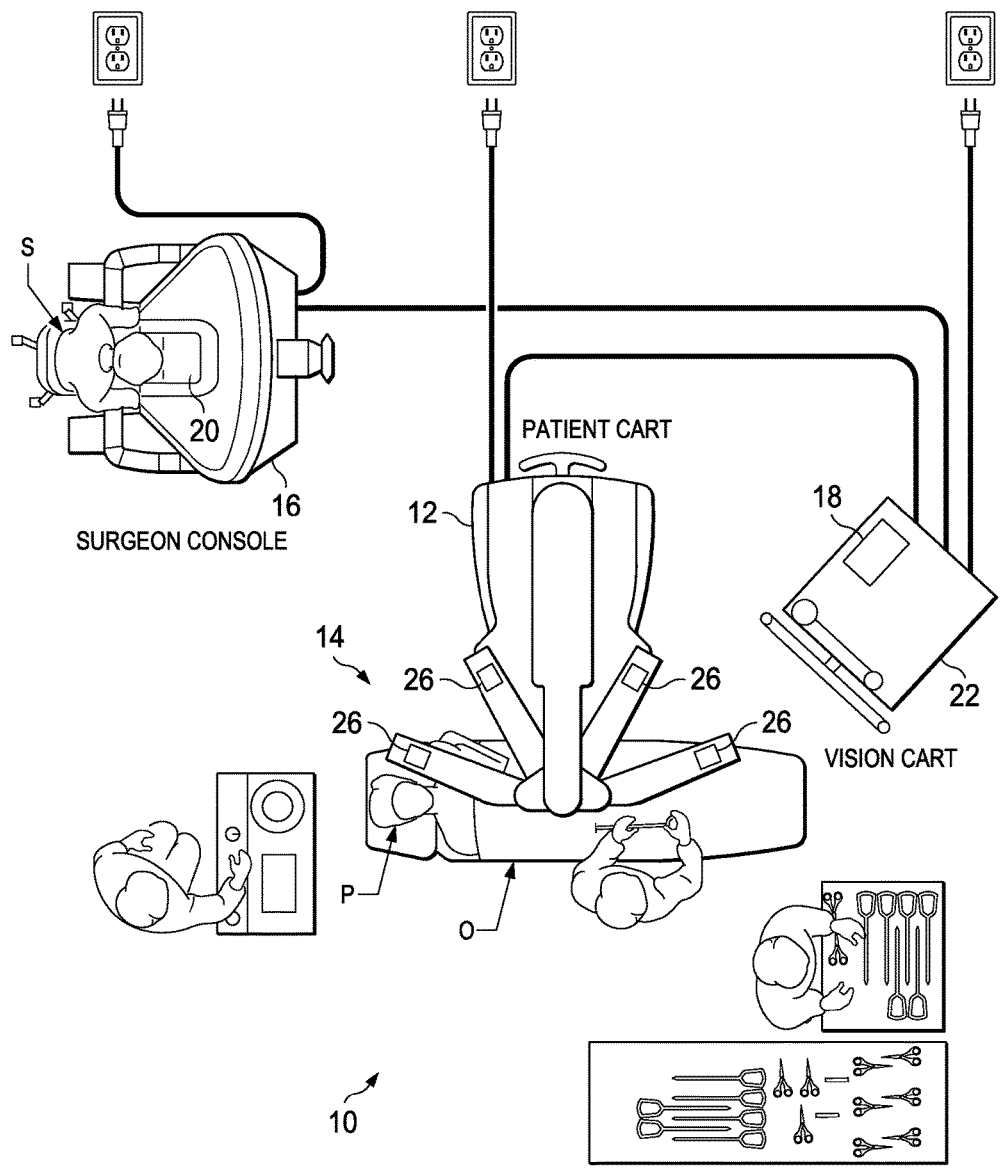
FIG. 1A illustrates an exemplary teleoperational medical system according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description, numerous specific details are set forth in order to provide a thorough understanding of the disclosed embodiments. However, it will be obvious to one skilled in the art that the embodiments of this disclosure may be practiced without these specific details. In other instances, well known methods, procedures, components, and circuits have not been described in detail so as not to unnecessarily obscure aspects of the embodiments of the disclosure.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. The numerous iterations of these combinations will not be described separately. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment can be used or omitted as applicable from other illustrative embodiments. For simplicity, in some instances the same reference numbers are used throughout the drawings to refer to the same or like parts.

The present disclosure relates generally to a guided setup system for a teleoperational medical system that may be arranged to perform a robotic surgery. The guided setup system is configured to provide instructions for the non-sterile and sterile OR staff interacting with the different components of the teleoperational medical system.

It progresses through a series of prompts, in recommended order, in preparation for surgery. For example, the guided setup system may provide visual and auditory feedback to users at a teleoperational assembly touchpad interface, as well as complementary feedback on a vision cart touchscreen interface, so users may access the guidance information from a variety of locations within the operating room.

Despite its series of prompts, the guided setup allows for flexibility in following the instructions, such as allowing users to skip non-essential steps, using manual controls to perform the same actions, or performing steps in a non-standard order. In addition, the guided setup is aware of the state of the teleoperational medical system, and responds with appropriate guidance when users perform a variety of activities, including, for example, draping the arms, connecting cannulas, and installing instruments. It may also accommodate workflows where events may occur in a non-standard order, for example, when multiple people are involved in preparing the teleoperational medical system for surgery, or when advanced users choose to perform steps differently to accommodate their particular needs. It may also allow the users to change options at any point and allow the system to be deployed and stowed at non-standard times to accommodate user errors or unanticipated clinical situations. The exemplary guided setup system disclosed herein leads users through phases of draping, docking, and targeting the patient prior to surgery.

According to various embodiments, the guided setup provides instructions relating to a teleoperational system to guide instrument delivery and operation for minimally invasive medical procedures. Referring to FIG. 1A of the drawings, a teleoperational medical system for use in, for example, medical procedures including diagnostic, therapeutic, or surgical procedures, is generally indicated by the reference numeral 10. As will be described, the teleoperational medical systems of this disclosure are under the teleoperational control of a surgeon. In alternative embodiments, a teleoperational medical system may be under the partial control of a computer programmed to perform the procedure or sub-procedure. In still other alternative embodiments, a fully automated medical system, under the full control of a computer programmed to perform the procedure or sub-procedure, may be used to perform procedures or sub-procedures. As shown in FIG. 1, the teleoperational medical system 10 generally includes a teleoperational assembly 12 near or mounted to an operating table O on which a patient P is positioned. The teleoperational assembly 12 may be referred to as a patient-side manipulator (PSM). A medical instrument system 14 is operably coupled to and forms a part of the teleoperational assembly 12. An operator input system 16 allows a surgeon or other type of clinician S to view images of or representing the surgical site and to control the operation of the medical instrument system 14. The operator input system 16 may be referred to as a master or surgeon's console. One example of a teleoperational surgical system that can be used to implement the systems and techniques described in this disclosure is a da Vinci® Surgical System manufactured by Intuitive Surgical, Inc. of Sunnyvale, Calif.

The teleoperational assembly 12 and its medical instrument system 14 may include a kinematic structure of one or more non-servo controlled links (e.g., one or more links that may be manually positioned and locked in place, generally referred to as a set-up structure) and a teleoperational manipulator. (See, e.g., FIG. 2) The teleoperational assembly 12 includes a plurality of motors that drive inputs on the medical instrument system 14. These motors move in response to commands from a control system 22. The motors include drive systems which when coupled to the medical instrument system 14 may advance the medical instrument into a naturally or surgically created anatomical orifice. Other motorized drive systems may move the distal end of the medical instrument in multiple degrees of freedom, which may include three degrees of linear motion (e.g., linear motion along the X, Y, Z Cartesian axes) and in three degrees of rotational motion (e.g., rotation about the X, Y, Z Cartesian axes). Additionally, the motors can be used to actuate an articulable end effector of the instrument. The teleoperational assembly 12 may be configured and arranged to sense, such as detect, calculate, or otherwise determine the position of each motor and/or each arm. The teleoperational assembly 12 includes a user interface configured to receive information from and convey information to a user. In some embodiments, the user interface is a touchpad interface that may present information to the user during guided setup of the teleoperational medical system 10. The teleoperational assembly 12 includes elements 26, such as sensors, switches, encoders, and/or other components that sense the arrangement of components of the teleoperational assembly. The arrangement may include the presence or absence of components as provided in the examples below or may include the physical relative position of components. The control system 22 is operatively linked to the touchpad, sensors, motors, actuators, encoders, hydraulic flow systems, and other components of the teleoperational assembly 12, the operator input system 16 and to an image capture system 18. The image capture system 18 includes an image capture device, such as an endoscope that may be carried on the medical instrument system 14 of the teleoperational assembly 12, and related image processing hardware and software.

The operator input system 16 may be located at a surgeon's console, which is usually located in the same room as operating table O. It should be understood, however, that the surgeon S can be located in a different room or a completely different building from the patient P. Operator input system 16 generally includes one or more control device(s) for controlling the medical instrument system 14. More specifically, in response to the surgeon's input commands, the control system 22 effects servomechanical movement of the medical instrument system 14. The control device(s) may include one or more of any number of a variety of input devices, such as hand grips, joysticks, trackballs, data gloves, trigger-guns, hand-operated controllers, foot-operated controllers, voice recognition devices, touchscreens, body motion or presence sensors, and the like. In some embodiments, the control device(s) will be provided with the same degrees of freedom as the medical instruments of the teleoperational assembly to provide the surgeon with telepresence, the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, and the like).

The system operator sees images, captured by the image capture system 18, presented for viewing on a display system 20 operatively coupled to or incorporated into the operator input system 16. The display system 20 displays an image or representation of the surgical site and medical instrument system(s) 14 as generated by sub-systems of the image capture system 18. The display system 20 and the operator input system 16 may be oriented so the operator can control the medical instrument system 14 and the operator input system 16 with the perception of telepresence. The display system 20 may include multiple displays such as separate right and left displays for presenting separate images to each eye of the operator, thus allowing the operator to view stereo images.

Alternatively or additionally, display system 20 may present images of the surgical site recorded and/or imaged preoperatively or intra-operatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, and the like. The presented preoperative or intra-operative images may include two-dimensional, three-dimensional, or four-dimensional (including, e.g., time based or velocity based information) images and associated image data sets for reproducing the images.

The control system 22 includes at least one memory and at least one processor (not shown), and typically a plurality of processors, for effecting control between the teleoperational system 12, medical instrument system 14, the operator input system 16, the image capture system 18, and the display system 20. The control system 22 also includes programmed instructions (e.g., a computer-readable medium storing the instructions) to implement some or all of the methods described in accordance with aspects disclosed herein. While control system 22 is shown as a single contained element in FIG. 1, the system may include two or more data processing circuits with one portion of the processing optionally being performed on or adjacent the teleoperational assembly 12, another portion of the processing being performed at the operator input system 16, and the like. Any of a wide variety of centralized or distributed data processing architectures may be employed. Similarly, the programmed instructions may be implemented as a number of separate programs or subroutines, or they may be integrated into a number of other aspects of the teleoperational systems described herein. In one embodiment, control system 22 supports wireless communication protocols such as Bluetooth, IrDA, HomeRF, IEEE 802.11, DECT, and Wireless Telemetry.

The control system 22 also includes a user interface that is configured to receive information from and convey information to a user. In the embodiments described herein, the user interface is a touchscreen monitor that may present prompts, suggestions, and status update during the guided setup process. In some embodiments, the touchscreen monitor is disposed in a position in the operating room where it can be easily seen as a user sets up the teleoperational assembly 12. This may be within a sterile zone of the system. In contrast, the touchpad on the teleoperational assembly 12 may be disposed at a location outside the sterile zone, and may be accessed by a non-sterile person during the guided setup. In another embodiment, both the touchpad and the touchscreen monitor are in the sterile zone. While described as a touchscreen monitor, other embodiments include other user interfaces, including one or monitors or display screens, a keyboard, a computer mouse, rollers, buttons, knobs, and other user interfaces.

The guided setup disclosed herein may be one or more computer programs executed on the control system 22 for dynamically assisting a user with setup of the teleoperational assembly 12. In some embodiments, the guided setup is executed on any of a wide variety of centralized or distributed data processing architectures. It may also be implemented as a number of separate programs or subroutines, or may be integrated into a number of other aspects of the teleoperational systems described herein.

In some embodiments, the control system 22 may include one or more servo controllers that receive force and/or torque feedback from the teleoperational assembly 12. Responsive to the feedback, the servo controllers transmit signals to the operator input system 16. The servo controller(s) may also transmit signals instructing teleoperational assembly 12 to move the medical instrument system(s) 14 which extend into an internal surgical site within the patient body via openings in the body. Any suitable conventional or specialized servo controller may be used. A servo controller may be separate from, or integrated with, teleoperational assembly 12. In some embodiments, the servo controller and teleoperational assembly are provided as part of a teleoperational arm cart positioned adjacent to the patient's body.

The teleoperational medical system 10 may further include optional operation and support systems (not shown) such as illumination systems, steering control systems, eye tracking systems, fluid management systems such as irrigation systems and/or suction systems. In alternative embodiments, the teleoperational system may include more than one teleoperational assembly and/or more than one operator input system. The exact number of manipulator assemblies will depend on the surgical procedure and the space constraints within the operating room, among other factors. The operator input systems may be collocated or they may be positioned in separate locations. Multiple operator input systems allow more than one operator to control one or more manipulator assemblies in various combinations.

Figure 1B:
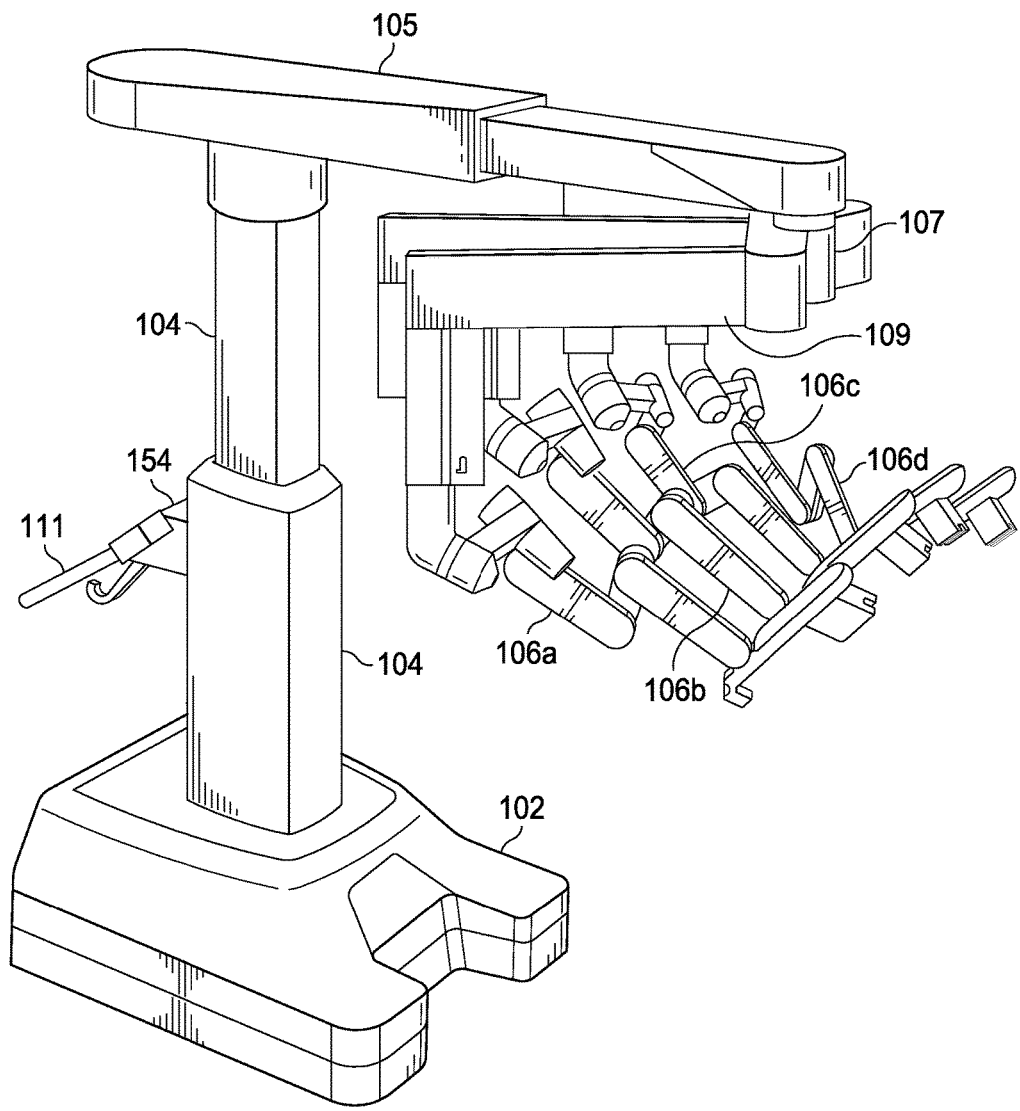
FIGS. 1B, 1C, and 1D illustrate exemplary components of a teleoperational medical system according to various embodiments of the present disclosure. In particular.

FIG. 1B shows an exemplary teleoperational assembly 100 (e.g., the teleoperational assembly 12 shown in FIG. 1A) according to one embodiment. The assembly 100 includes an automated and motorized setup structure that supports projecting arms, and may include a base 102 that rests on the floor, a telescoping support column 104 that is mounted on the base 102, a telescoping boom 105 that extends from the support column 104, and a platform portion as an orienting platform 107. The assembly 100 also includes support beams 109, and several arms 106 that support surgical tools (including portions of the image capture system 18). As shown in FIG. 1B, arms 106a, 106b, 106c, 106d are instrument arms that support and move the surgical instruments used to manipulate tissue. One of these arms 106 may be designated as a camera arm that supports and moves an endoscope.

FIG. 1E shows one of the arms 106 with an interchangeable surgical instrument 110 mounted thereon. The surgical instrument may be an endoscope mounted on the arm 106 designated as the camera arm. The endoscope may be a stereo endoscope for capturing stereo images of the surgical site and providing the separate stereo images to the display system 20. Knowledgeable persons will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm).

Figure 1C:
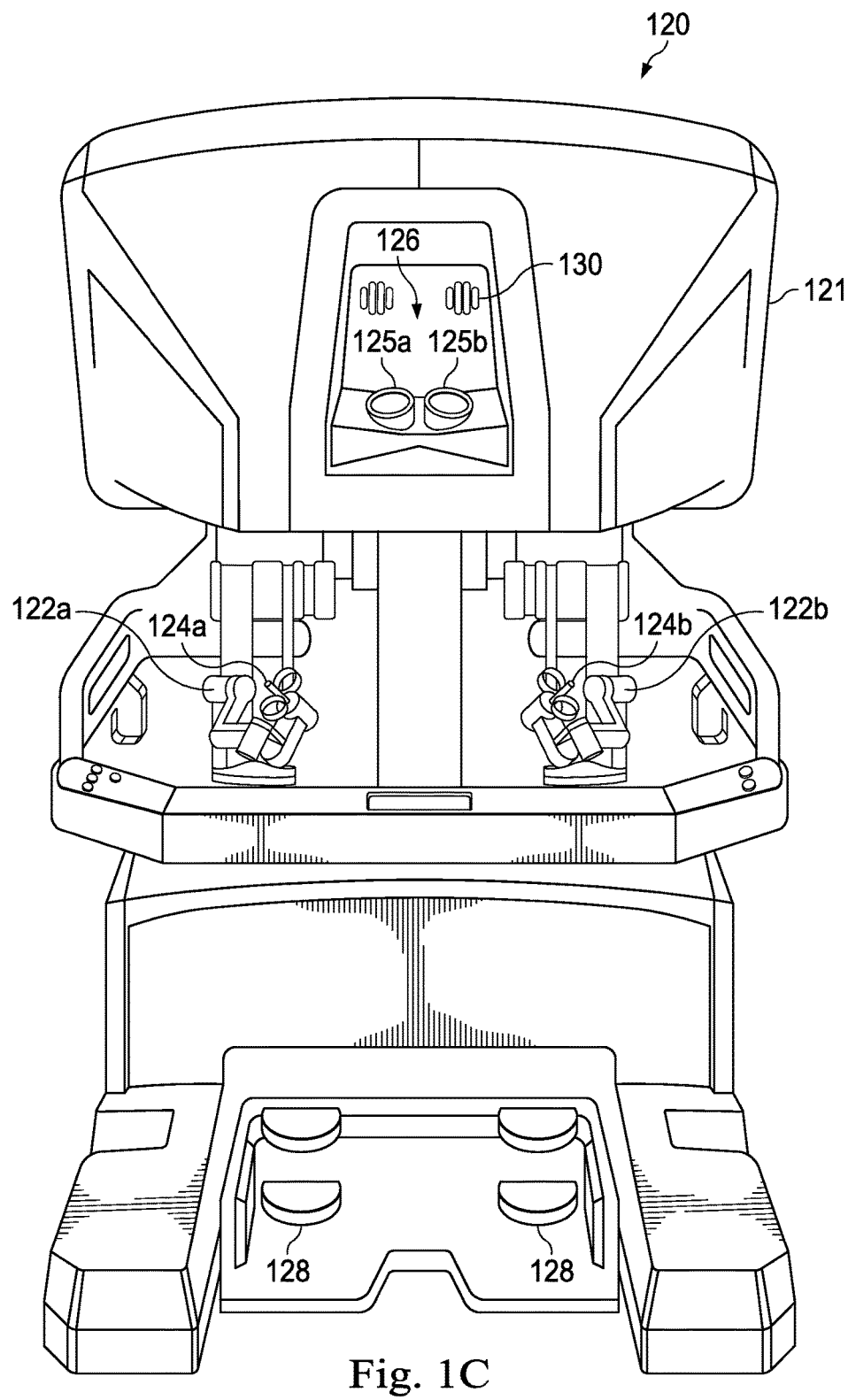

As is further illustrated in FIG. 1E, the instrument 100 includes an instrument interface 150 and an instrument shaft 152. In some embodiments, the teleoperational assembly 100 may include supports for cannulas that fix the instrument 110 with respect to the cannulas. In some embodiments, portions of each of the instrument arms 106 may be adjustable by personnel in the operating room in order to position the instrument with respect to a patient. Other portions of the arms 106 may be actuated and controlled by the operator at an operator input system 120 (as shown in FIG. 1C). The surgical instrument 110 associated with each arm 106 may also be controlled by the operator at the operator input system 120.

In more detail, the arm 106 includes a vertical setup 160 connected via a setup joint 162 to a distal-most setup link 164. A yaw joint 166 connects the distal-most setup link 162 to a parallelogram pitch mechanism 168. The parallelogram pitch mechanism 164 includes a plurality of pitch joints 170a, 170b, 170c enabling it move. A spar 172 connects to the parallelogram pitch mechanism 164 at a spar joint 174. Each of the setup joint 162, the yaw joint 166, the pitch joints 170a, 170b, 170c, and the spar joint 174 are controlled by motors, referenced herein as a setup joint motor, a yaw joint motor, pitch joint motors, and a spar joint motor. Accordingly, the arm 106 is configured to move in a completely motorized fashion. In this embodiment, the motors are under the control of the control system 22 and may be operated with motors of the other arms to take desired poses that may assist with draping, advancing over a patient, docking to surgical instruments, or storage, among others. In addition, encoders and sensors associated with each motor provide feedback to the control system 22 so that the control system senses or detects the position, status, and setup of the arm 106. In some embodiments, the spars 172 include sensors to detect the presence of surgical drapes on the arms 106.

The teleoperational assembly 100 also includes a helm 111 fixed relative to the base 102 on the support column 104 with a user interface for controlling the setup and operation. In some embodiments, the user interface is a touchpad 154 capable of accepting user inputs and providing graphical, textual, auditory, or other feedback. The touchpad 154 provides features for teleoperational assembly 100 activities such as preparation for draping, docking, or stowing to help the user minimize the space it takes up in the OR. The touchpad 154 also provides a means for system fault notification and recovery. In some embodiments, the touchpad 154 is disposed along the support column 104 and is configured to be viewed by a user in the operating room. In other embodiments, the touchpad or other user interface is disposed elsewhere. It may be wired or wireless and may be disposed within bag or elsewhere for sterile use. The touchpad 154 in this embodiment is configured to display informational data relating to status of the teleoperational assembly 100, information relating to particular surgical procedures, and information relating to the overall teleoperational medical system 10. In some embodiments, the touchpad 154 is a touchpad display interface that presents information and accepts user inputs. As such, a user may input control instructions, including setup instructions, at the touchpad.

FIG. 1C is a front elevation view of an operator input system 120 (e.g., the operator input system 16 shown in FIG. 1A). The operator input system 120 includes a console 121 equipped with left and right multiple degree-of-freedom (DOF) control interfaces 122a and 122b, which are kinematic chains that are used to control the surgical instruments 110 including the endoscope. The surgeon grasps a pincher assembly 124a, 124b on each of control interfaces 122, typically with the thumb and forefinger, and can move the pincher assembly to various positions and orientations. When a tool control mode is selected, each of control interfaces 122 is configured to control a corresponding surgical instrument and instrument arm 106. For example, a left control interface 122a may be coupled to control the instrument arm 106a and its associated surgical instrument 110, and a right control interface 122b may be coupled to the control instrument arm 106b and its associated surgical instrument 110. If the third instrument arm 106c is used during a surgical procedure and is positioned on the left side, then left control interface 122a can be switched from controlling the arm 106a and its associated surgical instrument 110 to controlling the arm 106c and its associated surgical instrument 110. Likewise, if the third instrument arm 106c is used during a surgical procedure and is positioned on the right side, then the right control interface 122a can be switched from controlling the arm 106b and its associated surgical instrument 110 to controlling the arm 106c and its associated surgical instrument 110. In some instances, control assignments between the control interfaces 122a, 122b and combination of arm 106a/surgical instrument and combination of arm 106b/surgical instrument may also be exchanged. This may be done, for example, if the endoscope is rolled 180 degrees, so that the instrument moving in the endoscope's field of view appears to be on the same side as the control interface the surgeon is moving. The pincher assembly is typically used to operate a jawed surgical end effector (e.g., scissors, grasping retractor, and the like) at the distal end of a surgical instrument 110.

Additional controls are provided with foot pedals 128. Each of foot pedals 128 can activate certain functionality on the selected one of instruments 110. For example, foot pedals 128 can activate a drill or a cautery tool or may operate irrigation, suction, or other functions. Multiple instruments can be activated by depressing multiple ones of pedals 128. Certain functionality of instruments 110 may be activated by other controls.

The surgeon's console 120 also includes a stereo image viewer system 126 (e.g., the display system 20 shown in FIG. 1A). Stereo image viewer system 126 includes a left eyepiece 125a and a right eyepiece 125b, so that the surgeon may view left and right stereo images using the surgeon's left and right eyes respectively inside the stereo image viewer system 126. Left side and right side images captured by endoscope 112 are outputted on corresponding left and right image displays, which the surgeon perceives as a three-dimensional image on a display system (e.g., the display system 20 shown in FIG. 1A). In an advantageous configuration, the control interfaces 122 are positioned below stereo image viewer system 126 so that the images of the surgical tools shown in the display appear to be located near the surgeon's hands below the display. This feature allows the surgeon to intuitively control the various surgical instruments in the three-dimensional display as if watching the hands directly. Accordingly, the servo control of the associated instrument arm and instrument is based on the endoscopic image reference frame.

The endoscopic image reference frame is also used if the control interfaces 122 are switched to a camera control mode. In some cases, if the camera control mode is selected, the surgeon may move the distal end of endoscope 112 by moving one or both of the control interfaces 122 together. The surgeon may then intuitively move (e.g., pan, tilt, zoom) the displayed stereoscopic image by moving the control interfaces 122 as if holding the image in his or her hands.

As is further shown in FIG. 1C, a headrest 130 is positioned above stereo image viewer system 126. As the surgeon is looking through stereo image viewer system 126, the surgeon's forehead is positioned against headrest 130. In some embodiments of the present disclosure, manipulation of endoscope 112 or other surgical instruments can be achieved through manipulation of headrest 130 instead of utilization of the control interfaces 122.

Figure 1D:
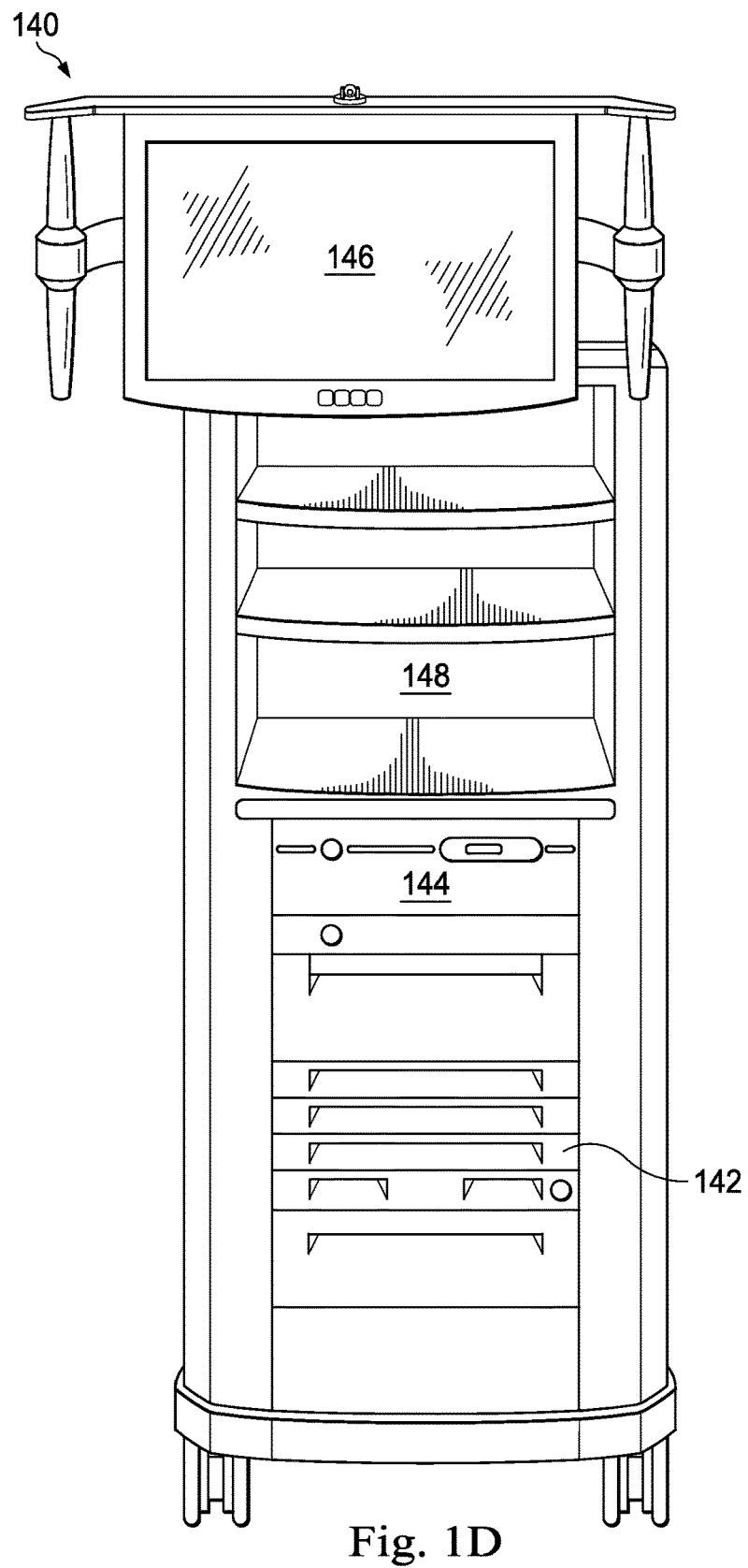

FIG. 1D is a front view of a vision cart component 140 of a surgical system. For example, in one embodiment, the vision cart component 140 is part of the medical system 10 shown in FIG. 1A. The vision cart 140 can house the surgical system's central electronic data processing unit 142 (e.g., all or portions of control system 22 shown in FIG. 1A) and vision equipment 144 (e.g., portions of the image capture system 18 shown in FIG. 1A). The central electronic data processing unit 142 includes much of the data processing used to operate the surgical system. In various implementations, however, the electronic data processing may be distributed in the surgeon console 120 and teleoperational assembly 100. The vision equipment 144 may include camera control units for the left and right image capture functions of the endoscope 112. The vision equipment 144 may also include illumination equipment (e.g., a Xenon lamp) that provides illumination for imaging the surgical site. As shown in FIG. 1D, the vision cart 140 includes an optional touchscreen monitor 146 (for example a 24-inch monitor), which may be mounted elsewhere, such as on the assembly 100 or on a patient side cart. The vision cart 140 further includes space 148 for optional auxiliary surgical equipment, such as electrosurgical units, insufflators, suction irrigation instruments, or third-party cautery equipment. The teleoperational assembly 100 and the surgeon's console 120 are coupled, for example, via optical fiber communications links to the vision cart 140 so that the three components together act as a single teleoperated minimally invasive surgical system that provides an intuitive telepresence for the surgeon.

The touchscreen monitor 146 may form a user interface that provides status and prompts during the guided setup process described herein. While a touchscreen monitor is shown, it is worth noting that other types of user interfaces may be used, including those described above with reference to the touchpad 154. It is worth noting that some guided setup processes receive no user inputs at the user interface because the system is arranged to sense or otherwise recognize when a setup step is complete. Accordingly, in some embodiments the user interface is merely a display that does not receive user inputs. Additional details and embodiments of the surgical system 10 are described in U.S. Patent Application Publication No. US 2013/0325033 A1 (filed May 31, 2013) and U.S. Patent Application Publication No. US 2013/0325031 A1 (filed May 31, 2013), both of which are incorporated herein by reference in their entirety.

Note that in some embodiments, some or all of the assembly 100 of the teleoperated surgical system can be implemented in a virtual (simulated) environment, wherein some or all of the image seen by the surgeon at the surgeon's console 120 can be synthetic images of instruments and/or anatomy. In some embodiments, such synthetic imagery can be provided by the vision cart component 140 and/or directly generated at the surgeon's console 120 (e.g., via a simulation module).

Not surprisingly, the teleoperated surgical system 10 described with reference to FIGS. 1A-1E may require some level of setup prior to performing a minimally invasive surgical procedure. The exemplary embodiments disclosed herein may utilize all or a part of the guided setup process implemented by the central electronic data processing unit 142. The guided setup process may be a machine augmented and configuration dependent guided walkthrough. It may dynamically recognize inputs and provide guidance and prompts to users to perform various setup actions. The prompted setup actions are based on the user's prior selected inputs, and based on sensed system configurations of the teleoperational assembly 100. For example, the system may sense the position of the arms 106, may sense whether an instrument, such as the endoscope is attached, whether the arms 106 are draped and in a sterile condition, and other sensed configurations. Because it takes into account the sensed teleoperational assembly configuration, the guided walk-through process may recognize when each setup step is complete through an automated process, when a setup step is complete through a manual process, when a user is intending to skip a setup step, and when a setup step does not need to be completed and need not be presented to a user. Accordingly, the guided setup may dynamically guide a user through the setup process to maintain a safe, yet efficient setup process that may differ even among similar types of surgeries. That is, the guided setup may have a different setup sequence among similar surgeries based on the sensed teleoperational assembly configurations and the setup that occurs when users perform setup steps out order. As such, many flexible setup options may be presented.

With visual prompts appearing on the touchpad 154 of the teleoperational assembly 100 and the touchscreen monitor 146 of the vision cart component 140, as well as auditory indication, the guided setup provides context sensitive step-by-step guidance to users. The guided setup may aid users in being efficient and effective during setup activities. However, the use of the guided setup is not required to achieve a reasonable setup, and may be simply ignored by a surgeon if desired. For example, users are free to perform setup activities in a different order if they choose, or they may choose a non-standard configuration for the system that might be appropriate for a particular clinical situation.

Because setup may involve users interacting with the controls at the teleoperational assembly touchpad 154, as well as with the vision cart touchscreen 146, relevant guidance is provided on both the teleoperational assembly touchpad 154 and the vision cart touchscreen monitor 146.

The guided setup process may be divided into three general setup phases, set forth in FIG. 2. These three identified phases are used to assist in explanation of the guided setup system, but are not intended to be treated as necessarily separate from the other phases, as the three identified phases overlap and share some common traits. The three general phases are the draping phase 202, the docking phase 204, and the targeting phase 206.

Each of the phases in FIG. 2 may encompass a number of states representing particular stages of the guided setup process. Each state may be associated with a step or a particular physical arrangement of the teleoperational assembly 100. The guided setup process advances the user from state to state until the setup process is complete. When the step or arrangement for a particular state has been met, the guided setup may proceed to the next state, defining the next setup process step.

Since the central electronic data processing unit 142 receives inputs indicative of sensed teleoperational assembly configurations, the central electronic data processing unit 142 recognizes when a state is complete. Therefore, the central electronic data processing unit 142 may advance the guided setup to the next state without any input at a user interface by a user. In addition, a user may override or skip one or more states or parts of states of the guided setup by simply placing the teleoperational assembly 100 in a configuration associated with a state farther along in the guided setup process. The central electronic data processing unit 142 will then sense the new configuration and identify the relevant state corresponding to the configuration. The context of the configuration determines what the system infers is the state and the next required action. If the system determines that a user appears to have skipped a state that is identified in the system as being especially important, the system will output a reminder. However, if the user continues after receiving the reminder, the system will continue and permit the user to move the next state based on the sensed configuration.

In the exemplary embodiment described herein, the states include associated instructions and prompts that are displayed on two user interface screens: the touchpad 154 on the teleoperational assembly 100 and the touchscreen monitor 146 on the vision cart component 140. However, other embodiments employ a single user interface, while yet other embodiments include even more user interfaces. In the exemplary embodiment shown, particular prompts associated with particular states are shown on one interface screen or the other depending on the state and the next action to be taken. For example, some prompts appear only on the touchpad 154 because the prompts relate to states for setup of the teleoperational assembly 100 that may be performed at a non-sterile field. Other prompts appear solely on the touchscreen monitor 146 because the prompts relate to states requiring attention in the sterile field. However, the prompts on both the touchscreen monitor 146 and the touchpad 154 are coordinated so that a user advances through the phases in FIG. 2 in a coordinated manner. Some embodiments include audio and voice prompts in addition to visual prompts. Some embodiments permit a user to customize preferences, such as setting the system in a silent mode.

Figure 3:
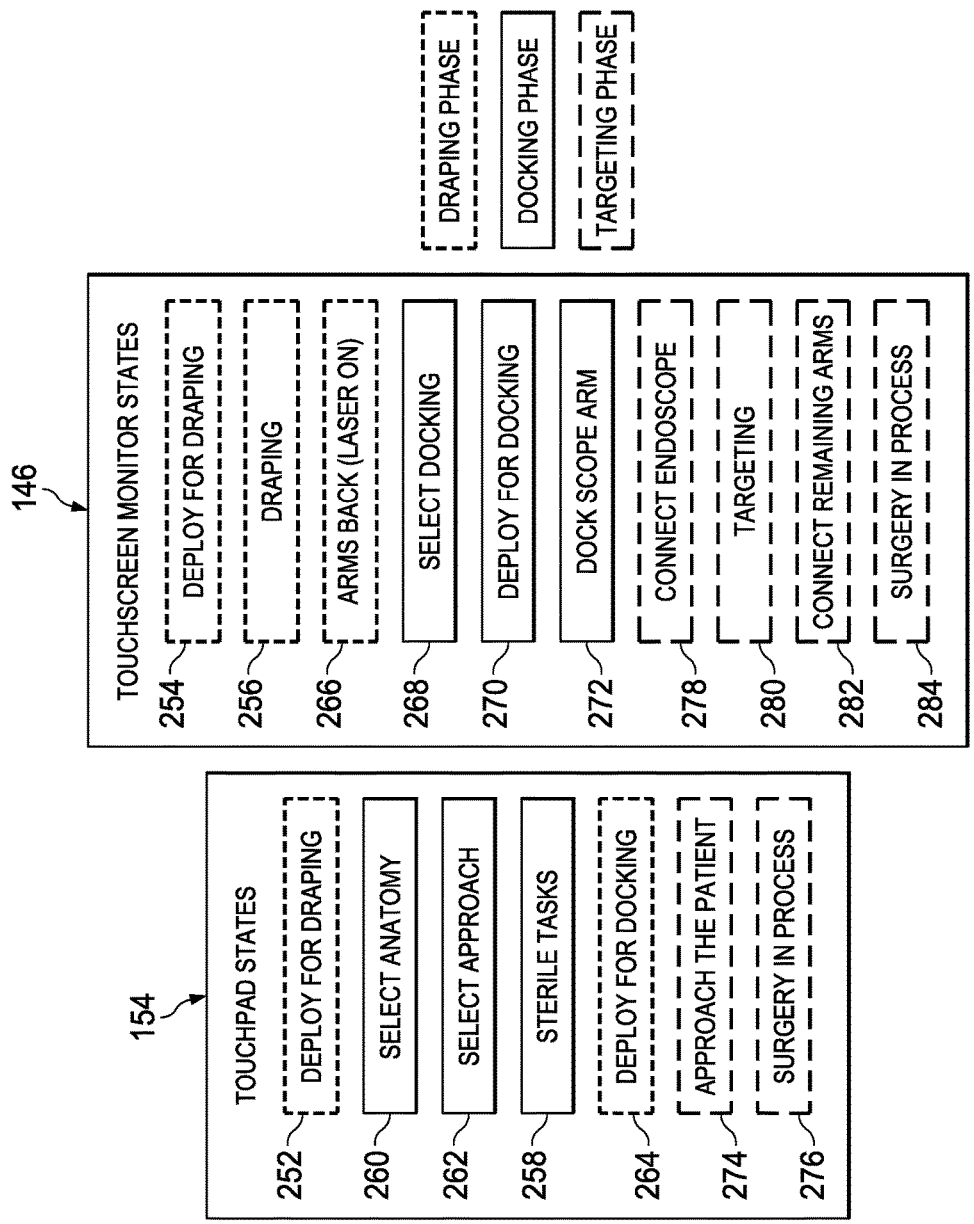
FIG. 3 illustrates various states of operation making up a part of the guided setup system disclosed herein according to one embodiment of the present disclosure.

FIG. 3 illustrates a series of exemplary states associated with screen prompts on both the touchscreen monitor 146 and the touchpad 154. The prompts associated with the states help a user advance through each phase (FIG. 2) to complete the guided setup of the teleoperational medical system 10. The column on the left lists a number of exemplary states having screen prompts that may be displayed on the touchpad 154 on the teleoperational assembly 100. The column on the right lists a number of exemplary states having screen prompts that may be displayed on the touchscreen monitor 146 on the vision cart component 140. In FIG. 3, the lines around each state correspond to one of the phases in FIG. 2. For example, the states in dotted lines are states forming the draping phase 202 in FIG. 2; the states in solid lines form the docking phase 204 in FIG. 2; and the states in dashed lines form the targeting phase 206 in FIG. 2. Here, the states are shown in the sequential order of the guided setup process. However, since the guided setup is dynamic and adaptable and is not held to a particular sequence, states may be skipped, may be different, and other states may be substituted for one or more of those shown in FIG. 3.

Still referring to FIG. 3, the draping phase may include, for example, a Deploy For Draping state 252 on the touchpad 154, a Deploy For Draping state 254 on the touchscreen 146, a Draping state 256, a Sterile Tasks state 258, and an Arms Back state 266. The docking phase may include, for example, a Select Anatomy state 260, a Select Approach state 262, a Select Docking state 268, a Deploy For Docking state 270, and a Dock Scope Arm state 272. The targeting phase may include an Approach The Patient state 274, a Surgery In Process state 276, a Connect Endoscope state 278, a Targeting state 280, a Connect Remaining Arms state 282, and a Surgery In Process state 284.

The Deploy For Draping states 252, 254 and the Deploy For Docking state 270 each may correspond with particular poses of the column 104, the boom 105, the arms 106, and the orienting platform 107 of the teleoperational assembly 100. In addition, a stow state, not a standard part of the guided setup routine, may also correspond with a particular pose of the column 104, the boom 105, the arms 106, and the orienting platform 107 of the teleoperational assembly 100. The stow state is essentially an at-rest state that is at least partially compact that may be used when the teleoperational assembly 100 is to be set aside for a period of time before, during, or after any part of the surgical process.

Figure 4:
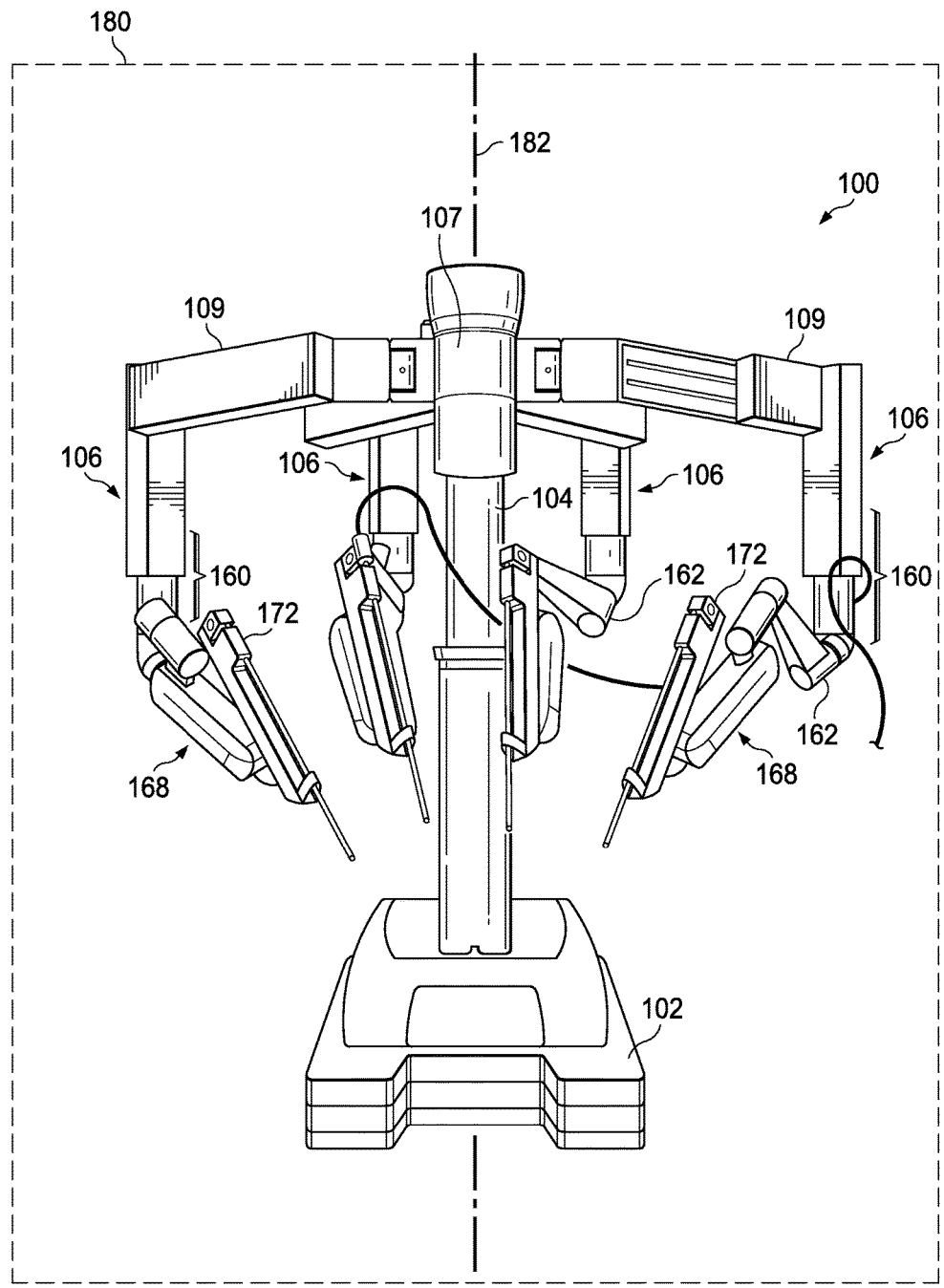
FIG. 4 illustrates the exemplary teleoperational assembly of FIG. 1B in a preset and automatically assumed draping pose according to one embodiment of the present disclosure.
Figure 5A:
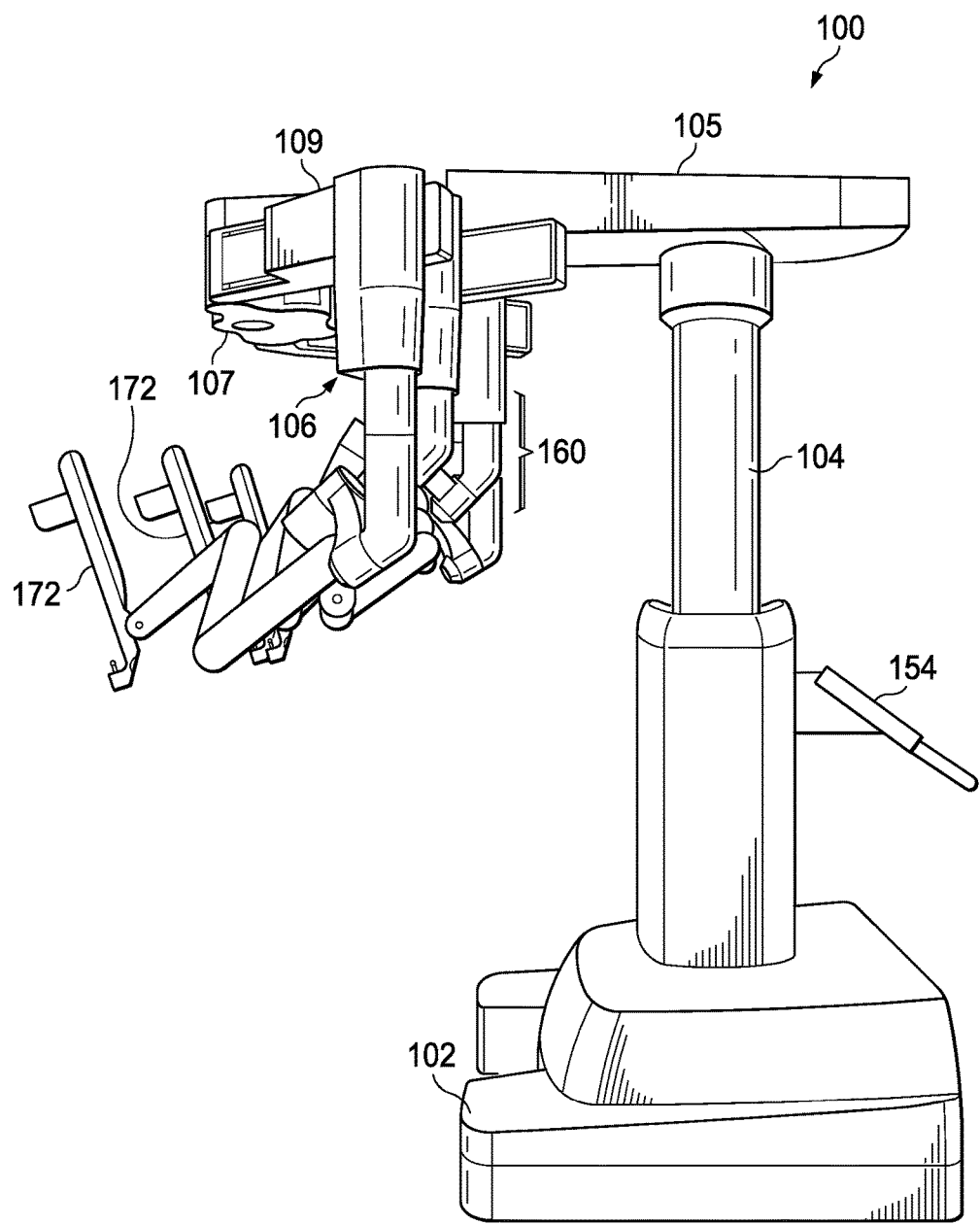
FIG. 5A illustrates the exemplary teleoperational assembly of FIG. 1B in a preset and automatically assumed docking pose according to one embodiment of the present disclosure.
Figure 5B:
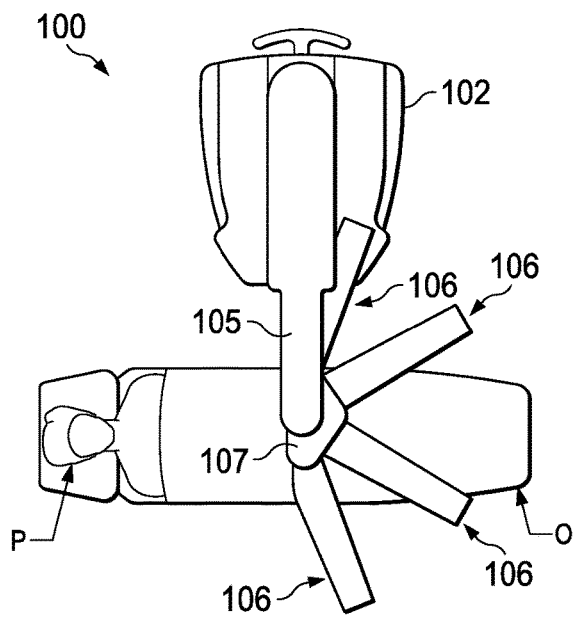
FIGS. 5B-5F illustrates the exemplary teleoperational assembly of FIG. 1B in various top views of preset and automatically assumed docking poses relative to a patient according to one embodiment of the present disclosure.
Figure 5C:
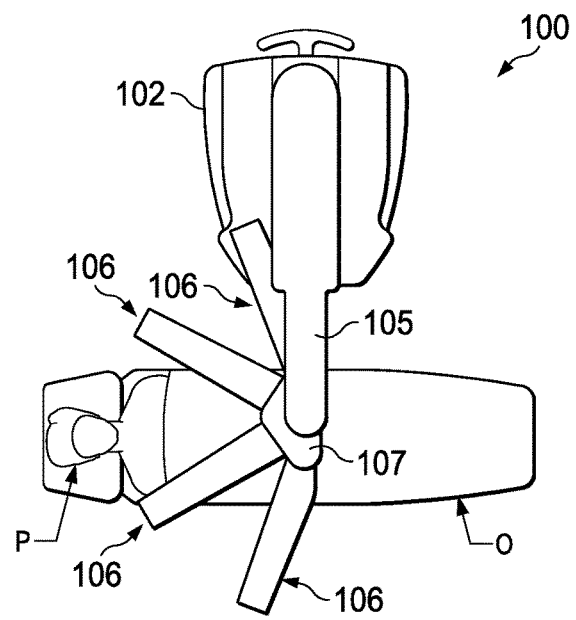
Figure 5D:
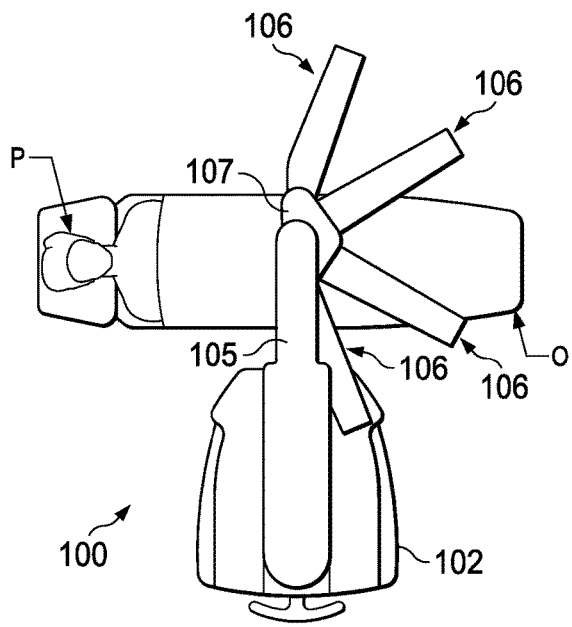
Figure 5E:
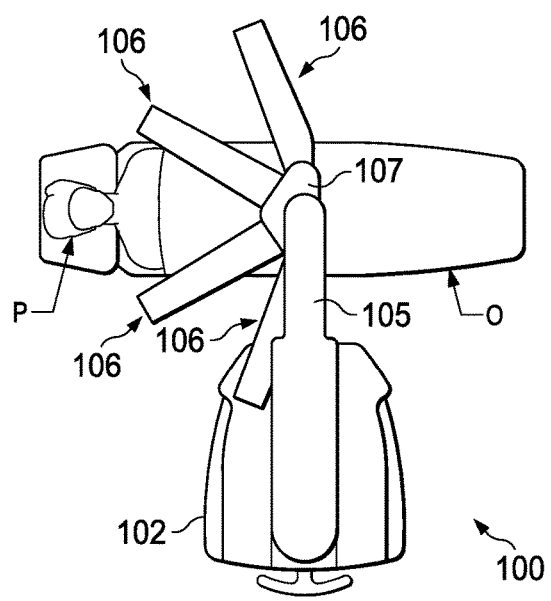
Figure 5F:
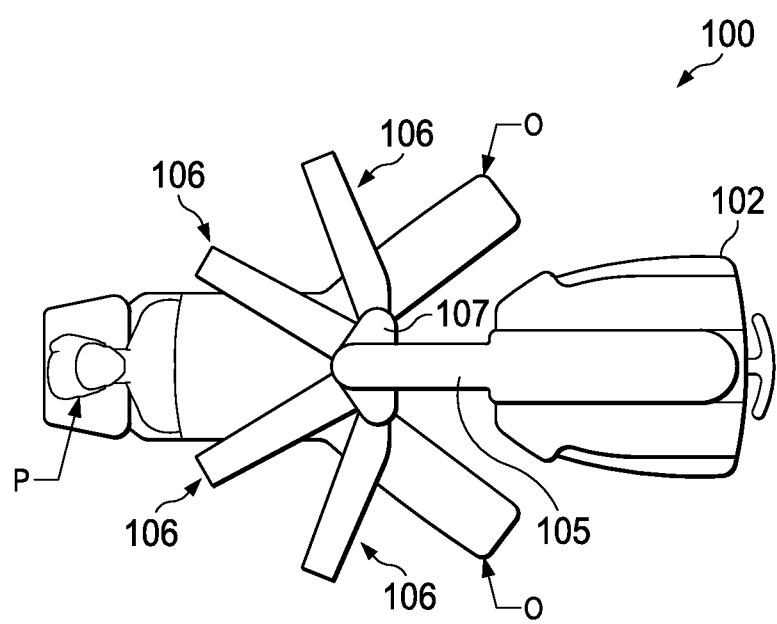
Figure 6:
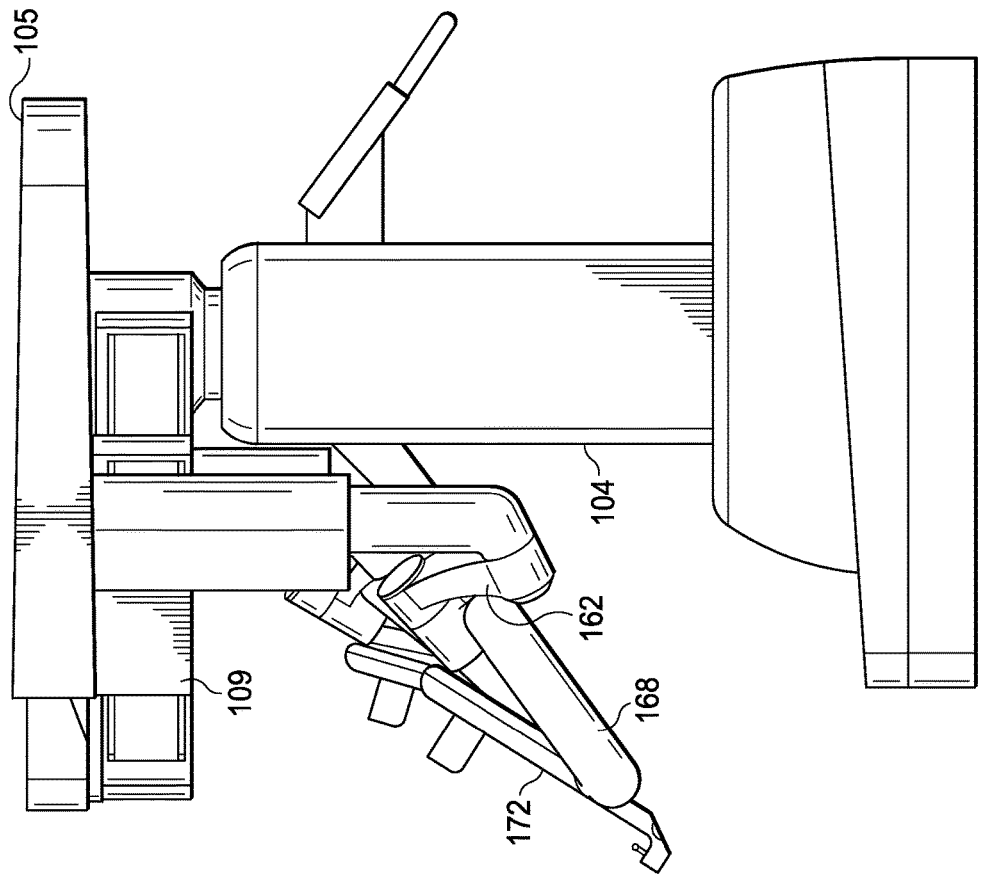
FIG. 6 illustrates the exemplary teleoperational assembly of FIG. 1B in a preset and automatically assumed stowed pose according to one embodiment of the present disclosure.

FIGS. 4, 5A-5F, and 6 show examples of different positions or postures relating to the different pre-established poses. For example, FIG. 4 shows the teleoperational assembly 100 in a draping position; FIGS. 5A-5F show the teleoperational assembly 100 in various docking positions; and FIG. 6 shows the teleoperational assembly 100 in a stowed position.

In the example shown, the touchpad 154 on the teleoperational assembly 100 may be used to input a command to deploy the column 104, the boom 105, the arms 106, and the orienting platform 107 to the pre-established positions. Other input devices are also contemplated for use to input the commands. Accordingly, in some embodiments, the touchpad 154 includes a Deploy for Draping button, a stow button, and a Deploy for Docking button, among others.

The deploy for draping position in FIG. 4 will be described with reference to planes through the column 104. Referring to FIG. 4, the plane parallel to the drawing sheet will be considered the coronal plane 180 and the plane directly normal to the coronal plane is the sagittal plane 182. The front of the teleoperational assembly 100 faces the direction of the sagittal plane 182, and the coronal plane extends directly to the sides of the teleoperational assembly 100.

FIG. 4 shows the teleoperational assembly 100 in the deploy for draping position. The deploy for draping position is a posture automatically taken by the teleoperational assembly when the arms 106 and/or column 104 are to be draped. As used herein, a posture automatically taken encompasses movement achieved by a single instantaneous input or through a continuous input such as a continuously pressed button. In continuous input embodiments, the teleoperational assembly moves only while the button is pressed, stopping all movement when the button is no longer pressed. This permits a user to immediately halt movement when necessary for safety or other reasons. In some embodiments, the deploy for draping position is taken only when a user inputs a command to take the deploy for draping position, such as by selecting a deploy for draping button.

As can be seen in this exemplary position, the column 104 extends so that the arms are at a height convenient to be accessed by a person of average height. In some embodiments, the spars 172 are disposed so that their upper ends are at a height in a range of about 54 inches to 66 inches. However, other heights are also contemplated. The vertical setups 160 are partially extended from the support beams 109 carried by the orienting platform 107. The arms 106 are each partially extended in the direction of the sagittal plane so that each element of the arms 106, including the vertical setup 160, the distal-most setup link 164, the parallelogram pitch mechanism 168, and the spar 172 may be individually draped with sterile drapes. The deploy for draping pose positions the spars 172 for sufficient inter-arm spacing prior to draping. The spacing permits a folded drape to be placed on an arm and used as a sterile barrier to activate arm control modes so that a sterile user may further extend the arm into available space in the operating room. In this embodiment, the spars 172 are posed to be spaced from adjacent spars slightly more at the top of the spars and slightly less at the bottom of the spars. Accordingly, the outermost spars 172 are angled the most relative to the sagittal plane 182. This may accommodate the additional drape material that may be placed over the tops of the spars 172. In addition, each spar 172 is angled in the sagittal plane direction with the top of the spar 172 being spaced further from the coronal plane than the bottom of the spar 172 so that the user may more easily connect the drapes to the spar 172. In some embodiments, the user may be able to see the top portion of the spar 172 so that the drapes can be properly disposed to activate drapery sensors on the spar 172 that recognize the presence of the drapes on the arms 106. The arms 106 in the draping position in FIG. 4 generally face in the forward or sagittal direction so that the user can access all arms 106 from the front, instead of accessing arms 106a and 106d extending to the sides. The exemplary draping position shown in FIG. 4 is partially compact to accommodate instances where the teleoperational assembly 100 is draped within an operating room that does not have unlimited space for access. In addition, the proximity of the arms adjacent each other provides sufficient space for draping while having the arms close enough together for efficient draping.

In an exemplary aspect, when a deploy for draping process is initiated, the central electronic data processing unit 142, which may include multiple control systems about the teleoperational medical system 10, controls the arms 106 to place them in a draping position. The draping position may be obtained via a series of sequential movements of the teleoperational assembly 100. For example, the sequential movements may include a boom movement, an arm deployment movement, and a vertical setup joint movement. The boom movement may include raising the boom to a preset height set for draping convenience. The arm deployment movement may then follow without additional input or may automatically follow as a result of a continuous input at a button, for example. The arm deployment movement may include extending the arms 106 and arranging the spars 172 in the manner discussed above. The vertical setup joint movement follows the arm deployment movement and includes adjusting the vertical setup joint 164 in the manner discussed above.

FIG. 5 shows the teleoperational assembly 100 in the docking position. The docking position is the posture taken when the user has selected the general anatomical region to be treated and the approach to the patient (e.g., the left or right side of the patient). With the teleoperational assembly 100 in the docking position, it can be moved over the patient. In this driving position, the arms are slightly retracted, the spars are oriented upright in preparation for docking to cannulae, the column 104 is extended to raise the boom 105 and arms 106 high above the patient table. In addition, the vertical setup 160 is lifted so that arms 106 are high enough to clear the patient when the teleoperational assembly is advanced over the patient. The deploy for docking process also adjusts the distal setup joint 162 for the selected anatomical region to be treated. This joint is intelligently set based on anatomy and approach direction to provide adequate clearance upon rollup while being close to the optimal setting for surgery. For example, an outer arm 106 that does not need to pass-over the patient can be deployed low for maximum instrument reach whereas an outer arm that has to pass-over the patient may be deployed at a medium height to ensure adequate patient clearance upon rollup. At the same time, depending on the anatomical region to be treated and the approach selected, the orienting platform 107 and the support beams 109 may also be controlled. In some embodiments, one or more joints may be passively controlled and un-motorized, while in other embodiments, all the joints are motorized and controlled for purposes of guided setup.

In an exemplary aspect, when a deploy for docking process is initiated, the central electronic data processing unit 142, which may include multiple control systems about the teleoperational medical system 10, controls the arms 106 to place them in a docking position. The docking position may be dependent on the anatomical region to be treated and on the patient approach. In some aspects, the deploy for docking process includes a series of sequential movements to obtain the docking pose. For example, the sequential movements may include an arm deployment movement, a vertical setup joint movement, a boom movement, a platform movement, and an arm re-deployment movement.

The arm deployment movement includes tucking the arms in a configuration so that the arms are relatively compact, with the spars 172 in a relatively vertical position. As indicated above, depending on the approach, (whether a patient's right side, a patient's left side, or a patient's leg approach, for example), the height of the arms are set a maximum height, with the setup joint angle optimized on a per arm basis to tradeoff clearance vs. reach. For example, the height of an arm that will not pass over the patient is deployed low for maximum instrument reach, and with the height of an arm that has to pass-over the patient is deployed at a medium clearance to provide sufficient reach while ensuring adequate patient clearance upon rollup.

When the arms are finished moving, the vertical setup joint movement takes place without a separate input. For example in continuous input embodiments, based on the same continuous input, the teleoperation assembly begins the vertical setup joint movement. In this movement, the vertical setup joint 160 retracts fully to raise the proximal portion of the arms to their highest elevation to provide clearance for the arms. When the vertical setup joint movement is complete, the system performs the boom movement without additional user input. That is using the same input, such as the continuous input, the system manipulates the boom. The boom movement may include raising the boom with the telescoping column 104. The platform movement follows the boom movement and includes rotating the platform to the target orientation. This is based on the selected approach and different platform movements are shown in FIGS. 5B-5F. After the platform movement, the arms 106 are redeployed to a convenient position for docking to the cannula associated with the patient. This may include placing the spars 172 in an upright position and orienting the distal-most setup link 164 to a preset condition associated with the selected approach and anatomical region.

Some embodiments permit a user to raise the boom to a height greater than the default height associated with any selected anatomical region and approach combination. This adjusted height may then be used as a floor for the remainder of the deploy sequence. Thus, when a patient is larger than a typical patient or when the patient is higher than a typical patient, the system may compensate all the movements in the deploy process by a simple adjustment of the height.

FIGS. 5B-5F show different docking positions that may be taken based on the user's inputs. For example, FIG. 5B shows an approach where the teleoperational assembly is approaching from the patient's left side and the treatment region may be in the lower anatomical regions of the patient. Fig. FIG. 5C shows an approach where the teleoperational assembly is approaching from the patient's left side and the treatment region may be in an upper anatomical region of the patient. FIG. 5C shows an approach where the teleoperational assembly is approaching from the patient's right side and the treatment region may be in a lower anatomical region of the patient. FIG. 5D shows an approach where the teleoperational assembly is approaching from the patient's right side and the treatment region may be in an upper anatomical region of the patient. FIG. 5F shows an approach where the teleoperational assembly is approaching from the patient's legs and the treatment region may be in a lower anatomical region of the patient.

FIG. 6 shows the teleoperational assembly 100 in the stow position. The compact stow position minimizes the space occupied by the teleoperational assembly in the operating room. Accordingly, in this position, all the arms 106 are tightly compacted against the column 104, the boom 105 is retracted as far as possible while accommodating the arms 106, and the column 104 is fully telescoped to make the teleoperational assembly as small as possible. Here, the orienting platform is rotated to allow the support beams 109 to extend from the orienting platform 107 in the rearward direction so that they have a minimal footprint.

In an exemplary aspect, when the stow process is initiated, the central electronic data processing unit 142, which may include multiple control systems about the teleoperational medical system 10, places the teleoperational assembly 100 in the stow position. This may be done as discussed above through a continuous input, or may occur through a single instantaneous input. In some aspects, the stow position is achieved via a series of sequential movements. For example, the sequential movements may include a platform movement, a vertical setup joint movement, an arm retract movement, and a boom movement.

The platform movement includes rotating the platform to a straight forward facing position. The vertical setup joint movement raises the vertical setup joint 164 to move the arms close to the boom. The arm retract movement then retracts the arms 106 so that the arms are laterally packed together, with two arms 106 on each side of the column 104. The boom movement then fully lowers the boom to a compact position, to create a small, compact footprint in the operating room. In a preferred embodiment, the arms 106 are positioned in an arrangement to fit within the footprint of the base 102.

Some embodiments result in a staggered arrangement that includes a second arm, such as arm 106b, being disposed in front of the column, its adjacent, first arm, such as arm 106a, flexed and disposed close by, the with a third arm, such as arm 106c, pushed all the way back and against the right side the column 104, and a fourth arm, such as arm 106d, flexed close the third arm and rotated inward.

Some embodiments include a separate sterile stow position. This position is also a position that minimizes the footprint, but is intended to accommodate the column 104 and arms 106 while they are covered with sterile drapes. In this position, the arms 106 are brought together in a manner that minimizes their obtrusiveness in the operating room, but still maintains the sterile drapes in a clean and undamaged condition. The sterile stow position, therefore may be the stow position when the teleoperational system 10 detects that the arms 106 and/or column 104 are covered in sterile drapes.

In some embodiments, the central electronic data processing unit 142 controls the movement of the column 104, the boom 105, the arms 106, and the orienting platform 107 by controlling the motors associated with each to move them to the desired positions. In some embodiments, the teleoperational assembly 100 includes its own supervisor and controllers so the deploy for draping, deploy for docking, and stow functions can be performed even when the teleoperational assembly 100 is used standalone (e.g. preparing for transport). In response to a command initiated at a user interface, such as the touchpad 154, supervisor logic in the central electronic data processing unit 142 outputs control signals to move the column 104, the boom 105, the arms 106, and the orienting platform 107 into the desired poses. In some aspects, the central electronic data processing unit 142 includes algorithms for sequencing or otherwise coordinating the motion of the arms 106 in a manner that proactively avoids collisions of arms and setup joints with the column. In some aspects, the central electronic data processing unit 142 monitors the joint motion during automated moves to mitigate collisions with objects, such as an operation table, for example. As explained below, the pre-established poses may be associated with different phases or states of the guided setup system.

Figure 7A:
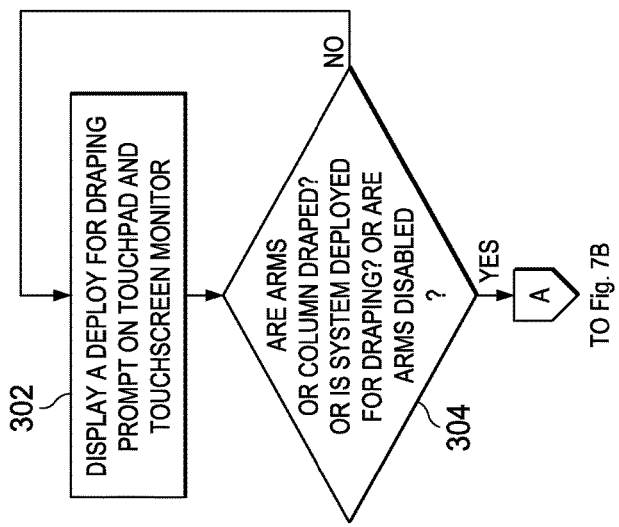
Figure 7B:
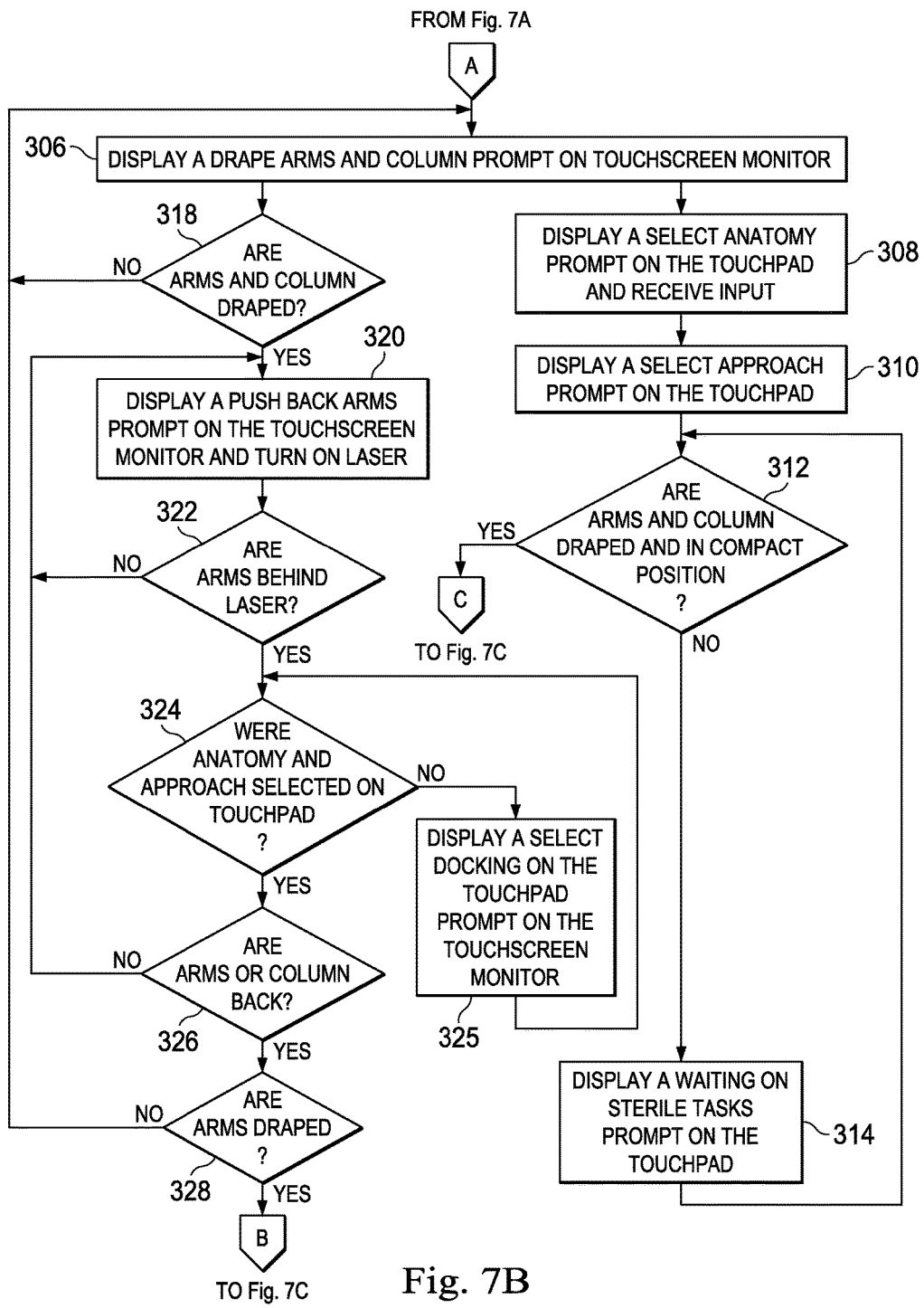

FIGS. 7A-7C show an exemplary method of using a guided setup performed by the teleoperational medical system 10. The method in FIG. 7 begins by displaying the prompts of the guided setup in the draping phase 202 in FIG. 2, then advances to the docking phase 204, and ultimately advances through the targeting phase 206. In some exemplary embodiments, the touchpad 154 includes a selectable guided setup feature button that initiates the process. Accordingly, after the user selects or initiates the guided setup, the system prompts the user to complete the various steps in the draping phase.

Figure 8:
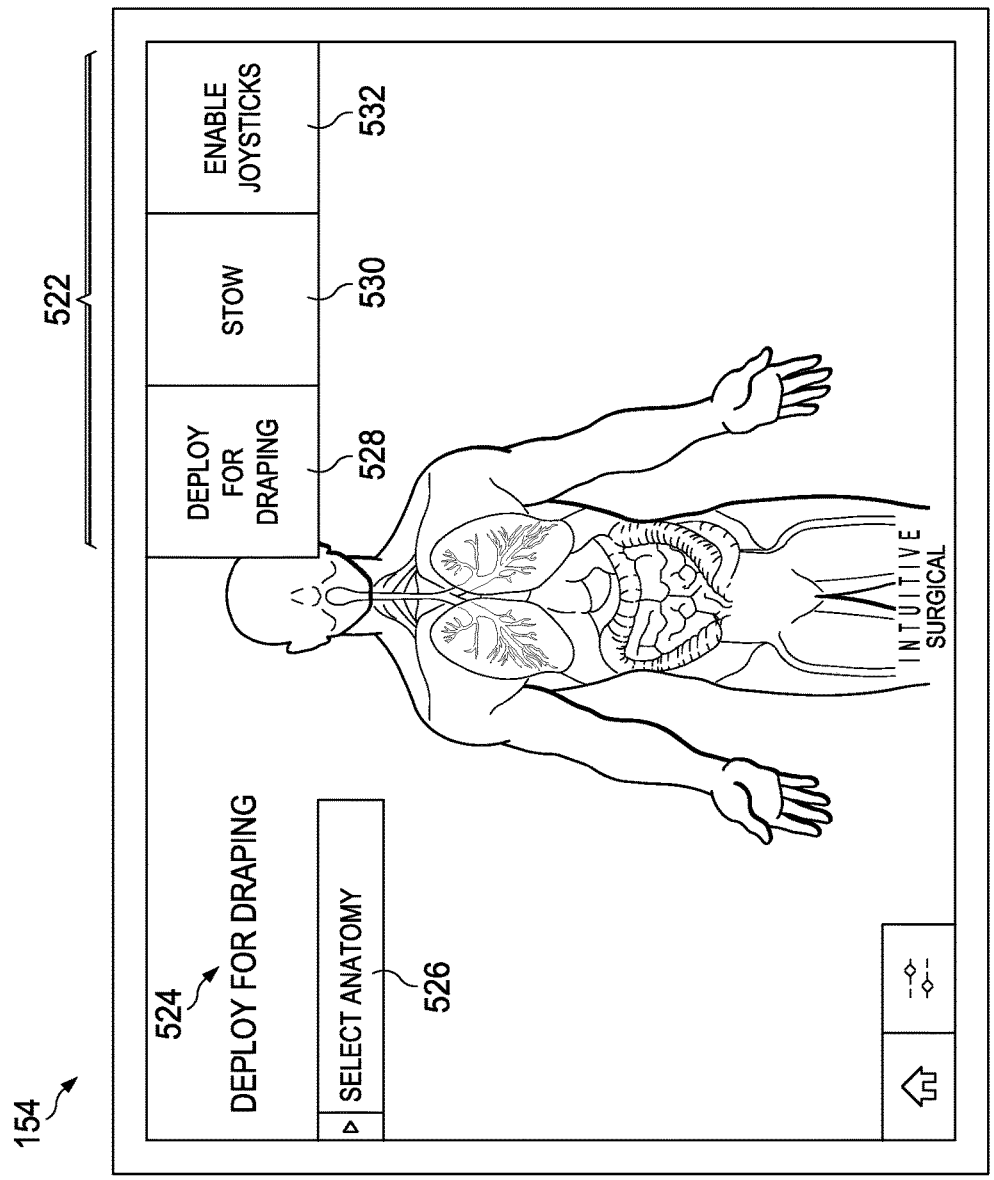
FIG. 8 illustrates an exemplary screen image of a touchpad user interface during the guided setup according to one embodiment of the present disclosure.
Figure 9:
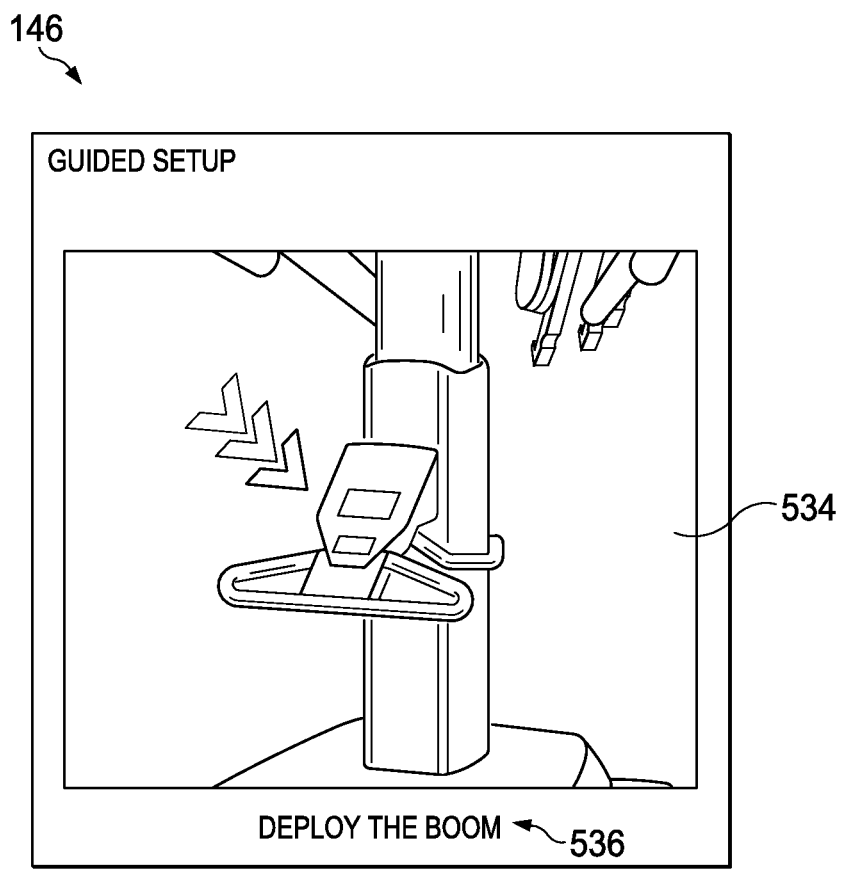
FIG. 9 illustrates an exemplary screen image of a touchscreen monitor user interface during the guided setup according to one embodiment of the present disclosure.

The method begins at 302 in the Deploy For Draping state 252, 254 by displaying a deploy for draping prompt on both the touchpad 154 and the touchscreen monitor 146. FIG. 8 shows an exemplary guided setup user interface on the touchpad 154 with the home tab selected. The user interface 220 includes, example shown, a plurality of selectable buttons 522, a guided setup screen prompt 524, and a select anatomy expandable menu 526. The selectable buttons 522 in this embodiment include a "deploy for draping" button 528, a "stow" button 530, and an "Enable Joysticks" button 532. FIG. 9 shows an exemplary guided setup user interface on the touchscreen monitor 146. As can be seen, it refers the user to the touchpad 154 on the teleoperational assembly 100 to initiate the guided setup and deploy the teleoperational assembly 100 (FIG. 1B) for draping. The touchscreen monitor 146 includes an explanatory image 534 and a text prompt 536. The touchscreen monitor 146 may also perform other functions or may be in a state of rest. In some embodiments, the both touchscreen monitor 146 and the touchpad 154 may be in a similar state, and may display a similar prompt.

Referring to FIG. 8, the user has the option to press the deploy for draping button 528 to initiate the automatic process of deploying the column 104, the boom 105, the arms 106, and the orienting platform 107 in the deploy for draping configuration shown in FIG. 4. In some embodiments, the column 104, the boom 105, the arms 106, and the orienting platform 107 move only while the button 528 is pressed or touched on the touchpad 154. This may enable the user to stop movement of the column 104, the boom 105, the arms 106, and the orienting platform 107 simply by removing a finger from the button 528. When the button is pressed, the central electronic data processing unit 142 generates and sends command signals to the teleoperational assembly 100 that also avoids arm collisions or contact as explained above.

The user also has the option to select the stow button 530. This would automatically deploy the teleoperational assembly 100 to the stew position shown in FIG. 6. Again, movement may occur only while the button 530 is pressed or touched on the touchpad 154.

In preferred embodiments, the teleoperational system 10 is configured to recognize via sensors or switches when sterile drapes are properly installed on any of the support column 104, the boom 105, and arms 106. It is also configured to recognize via sensors, encoders, or other devices, the position of the support column 104, the boom 105, and arms 106.

At 304 in FIG. 7A, the central electronic data processing unit 142 queries whether any of the arms 106 are draped, whether the support column 104 is draped, whether the teleoperational assembly 100 is Deployed for Draping (meaning in the deployed for draping position shown in FIG. 4), or whether the arms 106 are disabled. If none of the listed conditions are met at 304, then there is no change in the system screens, and the touchpad 154 and touchscreen monitor 146 are maintained in the Deploy For Draping state 252, 254. As such, the touchpad 154 continues to display the "deploy for draping" prompt at 524 in FIG. 8. However, if any of the conditions are met, then the guided setup system can automatically advance to the next setup state without receiving a specific user input to advance the setup process.

As indicated above, the guided setup dynamically provides setup guidance to a user, but also permits the user to setup the system without following the guidance if desired. In this embodiment, the user may place the arms 106 into the position suitable for draping using the "deploy for draping" button, or alternatively, may manually begin the draping process regardless of the positions of the arms. Therefore, for example, if the user were to control the arms using the operator input system 120 (FIG. 1C) or were to manually grasp and displace the arms to arrange them in a position suitable for draping, the guided setup system still advances to the next state if the control system detects that one of the arms or the column is draped. Therefore, the system recognizes that the user has moved beyond the Deploy For Draping state 254, and is working in the Draping state 256. Accordingly, the arms 106 do not have to be in the optimal position achieved via the automatic deploy setting in order to recognize that the task may be suitably completed, and to advance from the Deploy For Draping state to the next state.

When the criteria in 304 are met, the central electronic data processing unit 142 controls the touchscreen monitor 146 to advance it from the Deploy For Draping state 254 to the Draping state 256, and it displays a "Drape arms and column" prompt at 306, as indicated in FIG. 7B. Since the touchscreen monitor 146 is disposed on the vision cart component 140 (FIG. 1C) so that the user can view the touchscreen monitor 146 while standing in front of or working on the teleoperational assembly 100, the drape arms and column prompt may be displayed on the touchscreen monitor 146.

Figure 10:
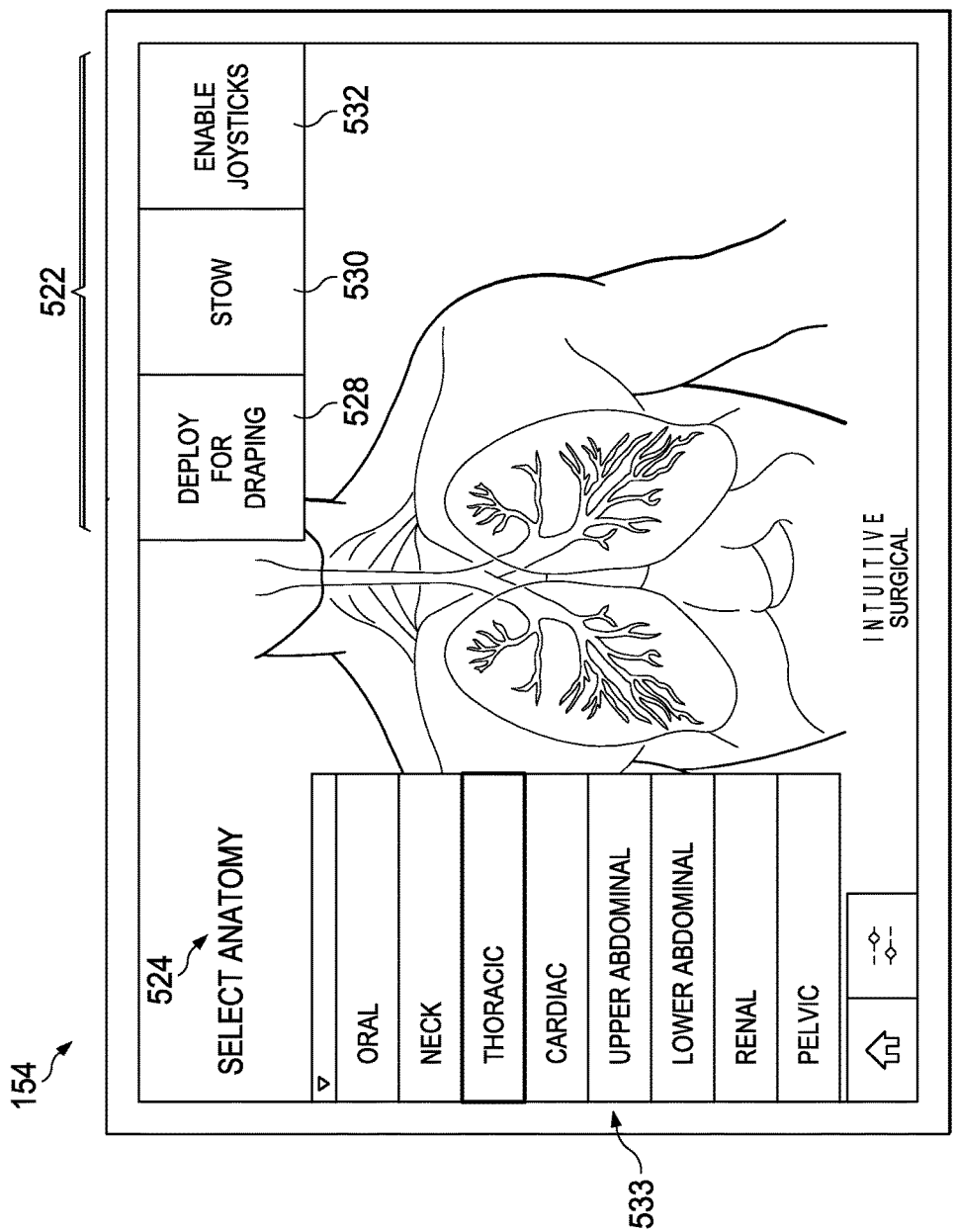
FIGS. 10 and 11 illustrate an exemplary screen image of a touchpad user interface during the guided setup according to one embodiment of the present disclosure.

At 308 in FIG. 7B, and when the touchscreen monitor 146 advances to the Draping state 256, the touchpad 154 begins the docking phase 204 in FIG. 3. Here, it leaves the Deploy For Draping state 252 and enters the Select Anatomy state 260 and displays a select anatomy prompt at the guided setup screen prompt 524. An example of this is shown in FIG. 10. In addition, the select anatomy button 526 in FIG. 8 automatically expands or opens without a user input to show a menu 533 of a plurality of selectable body regions where the surgery may occur. The user may input an anatomical region by selecting it from the menu 533 on the touchpad 154.

Figure 11:
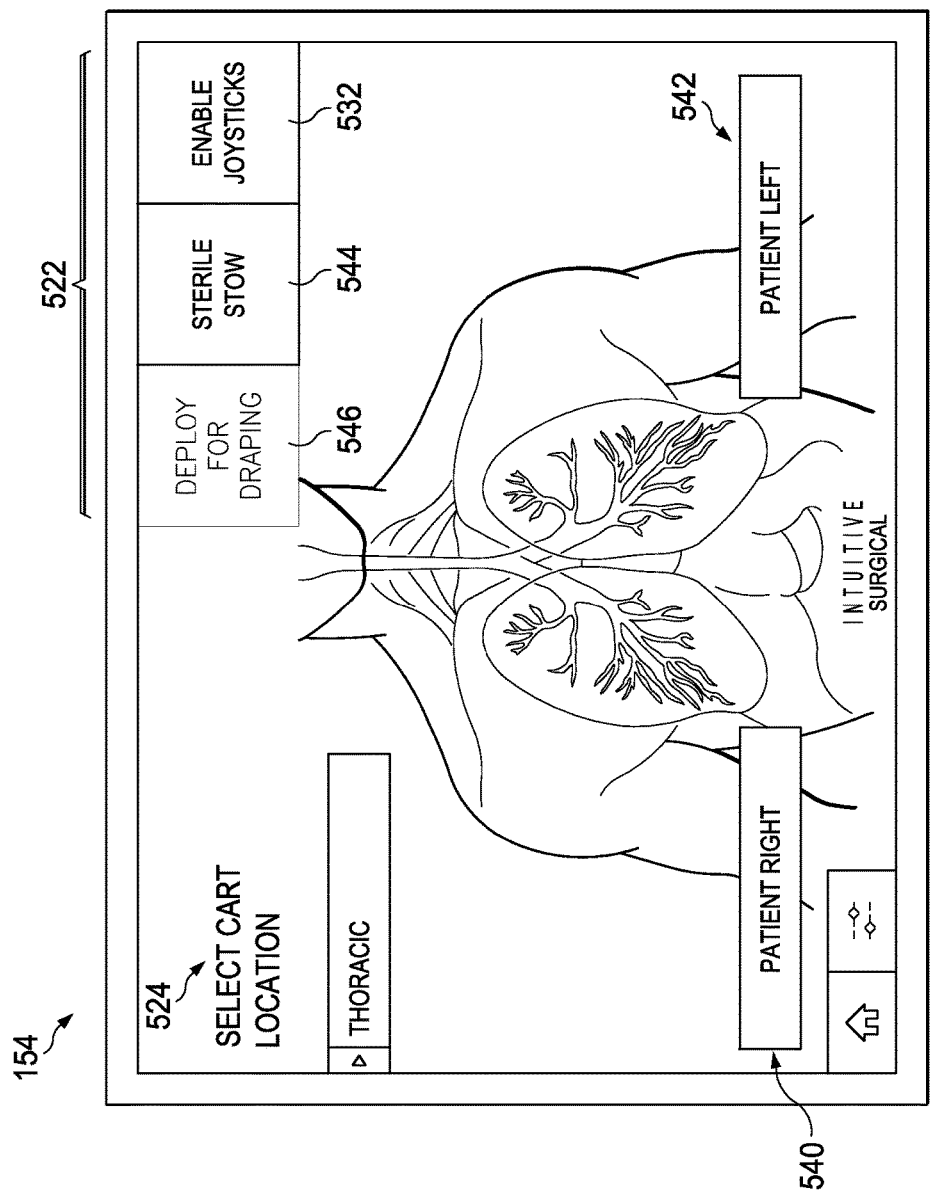

At 310 in FIG. 7B, and after a body region is selected, the touchpad 154 advances to the Select Approach state 262 and displays a select approach prompt as the guided setup screen prompt 524. An example of this is shown in FIG. 11. Depending on the selected anatomical region, a number of possible approaches are presented for selection. In FIG. 11, the possible selectable approaches are Patient Left button 540 or Patient Right button 542. FIG. 11 shows that if the Thoracic body region were selected at step 308, the selectable approaches may be limited to patient right and patient left. It is worth noting that other anatomical regions may be treated using additional approaches. For example, if the Pelvic region were selected at 308, the selectable approaches may include patient right, patient left, and patient legs. The user may input the approach by selecting it on the touchpad 154.

Also in FIG. 11, the stow button 530 (FIG. 10) has changed to a sterile stow button 544 and the deploy for draping button has been changed to a Deploy for Docking button 546. In some embodiments, this change occurs as a result of installation of one or more drapes. The sterile stow may be selected after surgical drapes are placed on the column 104 or the arms 106. The sterile stow is a stow intended to reduce the overall footprint of the teleoperational assembly 100 while maintaining the drapes in an undamaged and a sterile condition. Accordingly, the sterile stow position may be less compact than the stow position shown in FIG. 6. As with the other automatic positions discussed herein, some embodiments may allow the column 104, the boom 105, the arms 106, and the orienting platform 107 to move only while the button 530 is pressed or touched on the touchpad 154. Other embodiments control the column 104, the boom 105, the arms 106, and the orienting platform 107 to move completely to the preset position after merely pressing on the button without maintaining pressure on the button.

At a step 312 in FIG. 7B, and after a user has selected an anatomy and an approach, the central electronic data processing unit 142 may query whether the arms 106 and column 104 are draped and in a compact position. That is, the guided setup system queries whether draping is complete. If not, then the system waits at 314. Here, the touchpad 154 may advance to the Sterile Tasks state 258 and display a waiting on sterile tasks prompt at the guided setup screen prompt 524. If the arms or column were already draped and in a compact position when the approach is selected at 310, or when the arms and column are draped at 314, the touchscreen 154 advances to the Deploy For Docking state 264. In this state, at 316 in FIG. 7B, the touchscreen 154 displays a deploy for docking prompt as the screen prompt 524. This is discussed further below.

As discussed above, the guided setup system is configured to bypass states that are not required or that may have already been completed. Accordingly, at 312, if the system senses that the arms and column are already draped and that the arms are in a compact position, the guided setup skips the sterile tasks state 258 and advances directly to the Deploy For Docking state at 316, without any actual user input at the teleoperational system 10. That is, the system detects that the arms and column have sterile drapes thereon, and detects the position of the arms. Therefore, without any additional input at the user interfaces, the system may bypass or skip the sterile tasks state 258 and move to the Deploy For Docking state.

Figure 12:
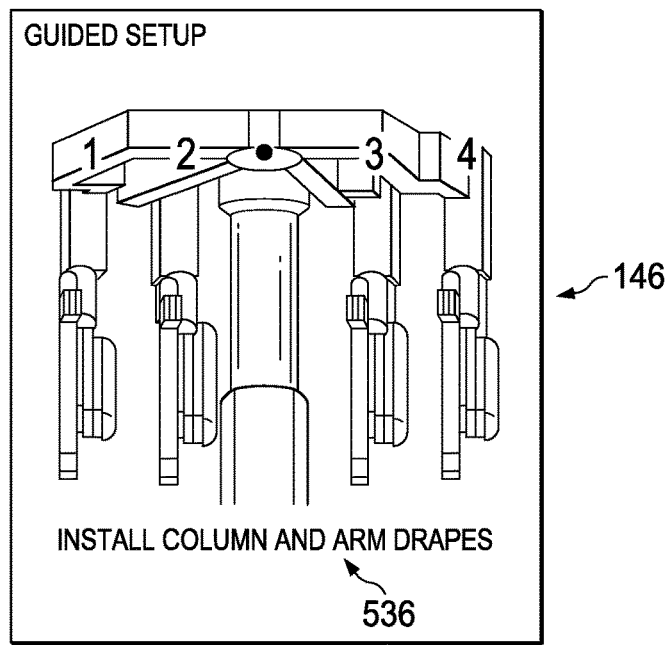
FIGS. 12 and 13 illustrate exemplary screen images of the touchscreen monitor user interface during the guided setup according to one embodiment of the present disclosure.

As mentioned above, certain actions may occur simultaneously on the touchpad 154 and the touchscreen monitor 146. Accordingly, at 306 in FIG. 7B, the touchscreen monitor 146 operates in the Draping state 256 and displays a drape column and arms prompt. The teleoperational medical system 10 provides feedback to the user at the vision cart touchscreen monitor 146, indicating which arms have been draped. Exemplary feedback may include, for example, an image of each arm and an indicator of whether it is properly draped. This indicator may be an identifying marker, such as a color, a shade, a number, or other indicator. Thus, the teleoperational assembly 100 may sense whether the drapes are properly installed on the arms and may present this to the user. FIG. 12 shows an image of each arm and the column as it may be displayed on the touchscreen monitor 146. The teleoperational system 10 is configured to sense and determine whether the arms or the column are draped without a prompt at the user interface. The guided setup prompt 536 on the touchscreen monitor 146 may be viewed by the sterile user as he or she works to install the drapes. As each drape is installed, the arm may be highlighted or otherwise marked to indicate that the arm is prepared for the next step in the setup process. In this embodiment, arms 1 and 2 are shown highlighted, and therefore are indicated as being properly draped.

At 318, the central electronic data processing unit 142 determines whether the arms and the column are properly draped. If they are not, the touchscreen monitor 146 continues to display the guided setup screen shown in FIG. 12.

Figure 13:
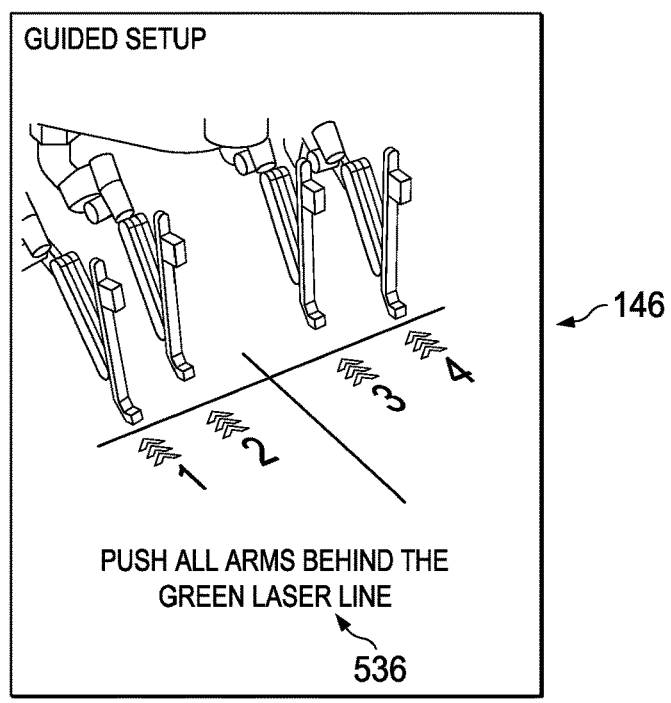

If at 318, the system senses that the arms and the column are properly draped, then the touchscreen monitor 146 advances to the Arms Back state 266, forming a part of the draping phase 202. Accordingly, the guided setup advances to 320 and automatically turns on a reference laser line and instructs the user to push all arms behind the reference laser line at 320. An example of this screen is shown in FIG. 13. In some embodiments, the system generates a voice prompt since the user's attention may be on the arms and not on the touchpad 154 or touchscreen monitor 146. Accordingly, the system may provide a voice prompt, such as "Push all arms behind the green laser line," for example. This position permits the user to later advance the teleoperational assembly 100 to the patient. The screenshot in FIG. 13 shows individual arms relative to a reference line corresponding with the actual laser reference line. As the actual arms 106 physically move behind the actual reference laser line, the arms in the image of FIG. 13 also displace rearward relative to the displayed line. As such, the user knows precisely which arms are sufficiently retracted and which are not. This is an example where the system uses a reminder to aid the efficiency of the overall workflow. Since the sterile user is already near the arms 106, that user is well suited to ensure the arms 106 are not blocking the laser. The laser will be used later by the non-sterile user when driving the teleoperational assembly 100 to the patient. If the arms 106 were left in a position that obstructs the laser, then the subsequent driving task may be delayed or lead to a suboptimal positioning of the teleoperational assembly 100.

At 322 in FIG. 7B, the central electronic data processing unit 142 queries whether the arms are properly disposed behind the reference laser line. If they are not, then the touchscreen monitor 146 continues to prompt the user at 320.

When all the arms are behind the laser reference line at 322, the central electronic data processing unit 142 queries whether the anatomical region and approach were already selected on the touchpad 154 (discussed with reference to 308 and 310 above). If at 324 the anatomical region and approach were not previously selected, then the touchscreen monitor 146 may display a reminder or prompt at 325 to direct the user to the touchpad 154 to perform steps 308 and 310 in FIG. 7B. That is, the touchscreen monitor 146 may advance to the Select Docking state 268 in FIG. 3 and instruct the user to enter the anatomical region and approach.

If the anatomical region and approach were already selected at 324 in FIG. 7B, then the guided setup system completely bypasses the Select Docking state 268, and the guided setup may advance directly to 326.

At 326, the central electronic data processing unit 142 again confirms that the arms are back behind the reference line. If the arms are not back at 326, then the system returns to the pushback arms prompt at 320. If the arms are back, the system again confirms that the arms are draped at 328. If the arms are not draped, the system returns to 306 which display the drape arms and column prompt. It's worth noting that there are actually two separate state machines running as part of the overall control system. One state machine governs the guidance provided on the touchpad 154 and the other state machine governs the guidance on the touchscreen monitor 146. Both state machines have access to the same input signals from the system but maintain their own finite states, since the states map more readily to distinct visual and audio feedback cues provided on the respective subsystems.

If the arms are back at 326 and the arms are draped at 328, then the touchscreen monitor 146 advances to the Deploy For Docking state 270, as indicated at 316 in FIG. 4B.

Figure 14:
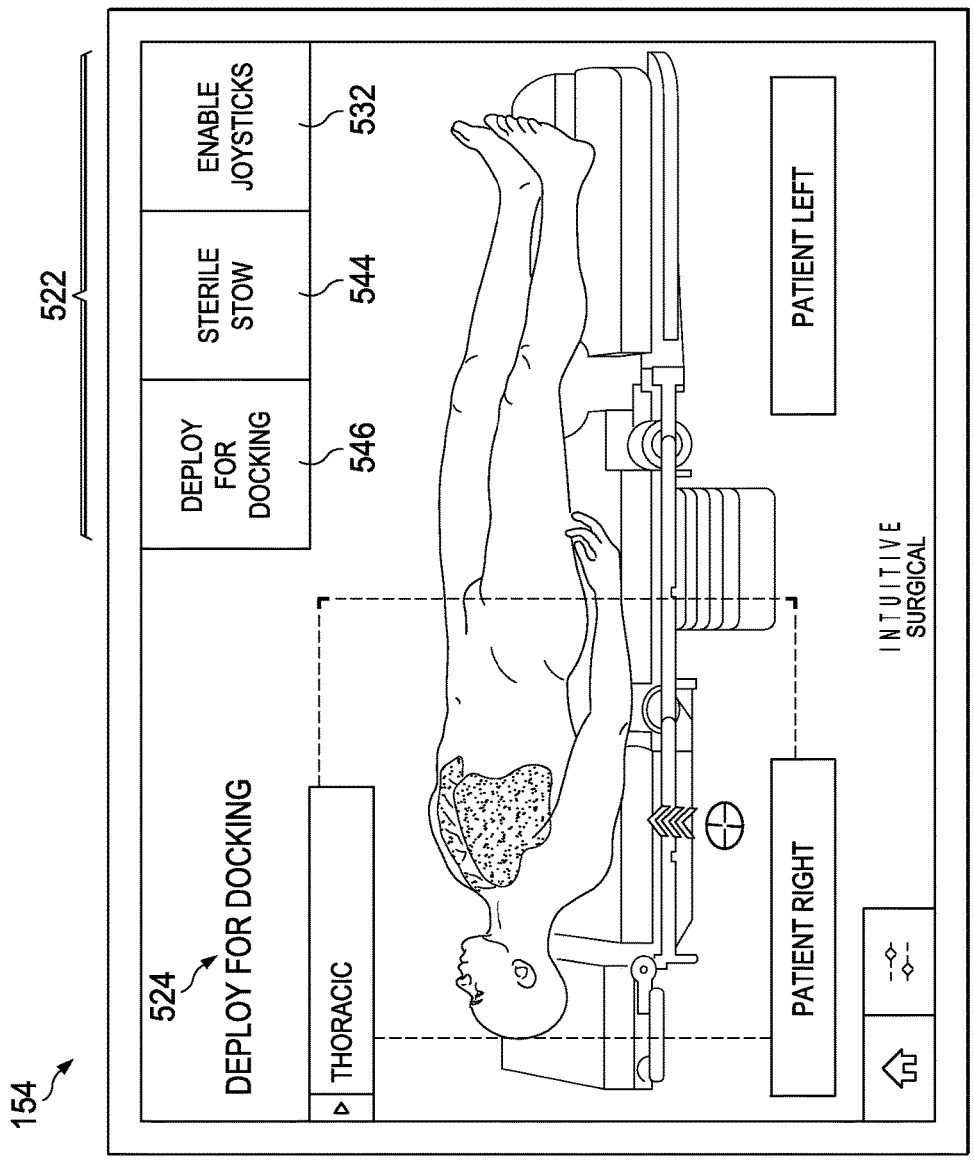
FIGS. 14 and 15 illustrate an exemplary screen image of a touchpad user interface during the guided setup according to one embodiment of the present disclosure.

The Deploy For Docking state on the touchscreen monitor 146 refers the user to the touchpad 154 which can control the arms 106 to place them in a docking configuration. At the same time, the Deploy For Docking state on the touchpad 154 provides a selectable deploy for docking button 546 in place of the deploy for draping button 528. This is shown in FIG. 14. In addition, FIG. 14 shows the selected approach and highlights the selected approach by providing an indicator, such as the target sign showing the selected approach relative to the patient.

A user may select the deploy for docking button 546, and in response, the teleoperational assembly 100 may move its column 104, boom 105, arms 106, and orienting platform 107 to a docking position that is dependent upon both the anatomical region selection and the approach selection. FIGS. 5A-5F discussed above show various deployed for docking positions that may be achieved at the Deploy For Docking state based on the selected anatomical region and approach.

Here, the user has the option to press the deploy for docking button 546 to initiate the automatic process of deploying the column 104, boom 105, arms 106, and the orienting platform 107 in the deploy for docking configuration shown in FIG. 5A-5F. In some embodiments, the column 104, boom 105, and arms 106 move only while the button 546 is pressed or touched on the touchpad 154. This may enable the user to stop movement of the column 104, boom 105, and arms 106 simply by removing a finger from the button 546. When the button is pressed, the central electronic data processing unit 142 generates and sends command signals to the teleoperational assembly 100 that also avoids arm collisions or contact as explained above, while moving the column 104, boom 105, arms 106, and the orienting platform 107 into the particular position which is dependent on both the selected anatomical region and the selected approach.

The guided setup system automatically deploys the teleoperational assembly to a position that is predetermined as an ideal spot for surgical procedures at the selected anatomical region and the patient approach. The predetermined position, for example, may be a position where the boom 105 and arms 106 are positioned away from range of motion limits, the vertical setups 160 are raised to provide maximum clearance upon rollup to the patient, the patient clearance setups 162 are positioned for suitable tradeoff between patient clearance and pitch range of motion for each arm 106, the arms 106 are positioned to minimize possible collisions between each other, and the manipulator arms are positioned to present their spars in an upright orientation to aid accessibility for docking. Some embodiments may include a menu including individual selectable surgical procedures instead of just the selectable anatomical region. This may enable the prestored docking position to have even additional options and prestored configurations. Some embodiments permit a user to input patient dimensions to provide an even more accurate docking configuration for a particular patient.

At 332 in FIG. 7B, the central electronic data processing unit 142 queries whether the arms are fully positioned in the deploy for docking position or whether the arms or gantry are disabled. If the arms are not fully in the deploy for docking configuration, or if the arms or boom are not disabled, then the touchscreen monitor 146 and the touchpad 154 display the deploy for docking prompt.

Figure 15:
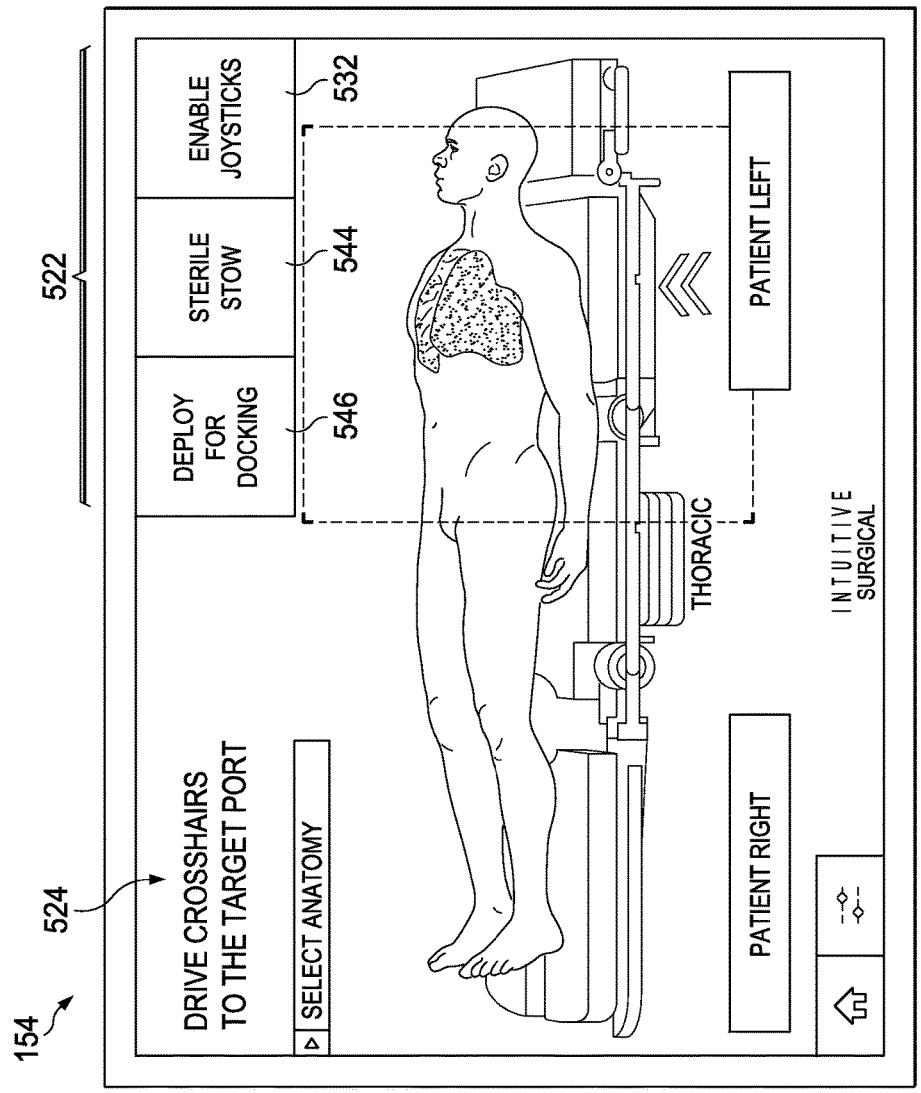

When at 332 the arms are fully deployed for docking or the arms are disabled, then, at 334 in FIG. 4C, the touchpad 154 advances to the Approach The Patient state 274 and instructions are displayed to drive, or advance the teleoperational assembly to the patient. This may include instructions to manually push the teleoperational assembly 100 to the patient or may have a motorized drive configured to advance the teleoperational assembly 100 to the patient. At this time, the central electronic data processing unit 142 turns on a targeting light on the orienting platform 107 that projects a target light, such as a target-shaped light downward from the boom 104 of the teleoperational assembly 100. In some embodiments, the target light is a cross-hairs that may be used as a reference to align the teleoperational assembly 100 over the patient. In one example, the Approach The Patient guided setup screen prompt 524 prompts a user to drive the crosshairs to the target port on the patient. FIG. 15 shows an example of the touchpad 154 when in the Approach The Patient state 274. As can be seen, the guided setup screen prompt 524 includes instructions to drive crosshairs to the target port. In the example shown in FIG. 15, the patient left was selected as the approach instead of the patient right.

Figure 16:
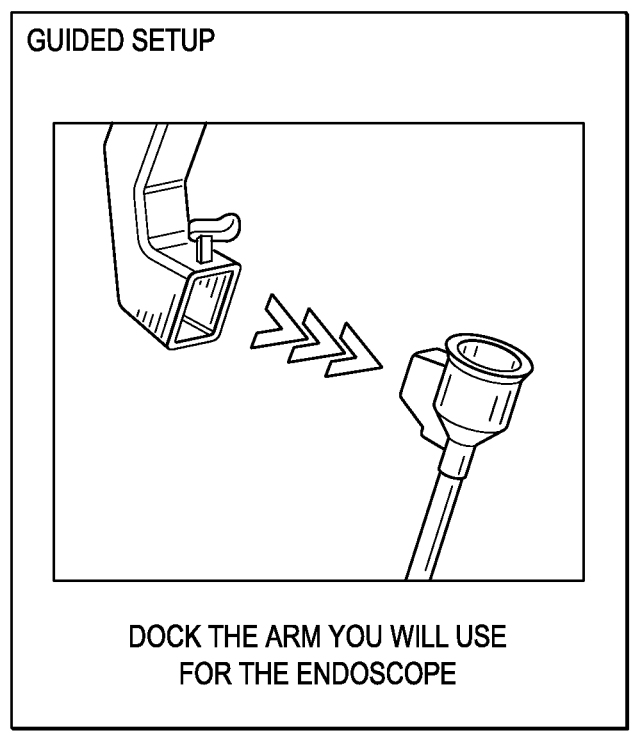
FIG. 16 illustrates an exemplary screen image of a touchscreen monitor user interface during the guided setup according to one embodiment of the present disclosure.

At 336, the touchscreen monitor 146 advances to the Dock Scope Arm state 272 and presents a prompt to the user to dock an endoscope on the designated endoscope arm. An example of this is shown in FIG. 16. At 337 in FIG. 7B, the central electronic data processing unit 142 queries whether the endoscope arm is attached to a cannula. If it is not, the prompt continues to display at 336. If it attached, the guided setup on the touchpad 154 advances to the Surgery In Process state 276 and the touchpad 154 indicates that a surgery is in process at 338. This ends the guided setup on the touchpad 154.

In the exemplary method described herein, the guided setup continues on the touchscreen monitor 146 and enters the Targeting phase 206 in FIG. 2. At 340, the touchscreen monitor 146 advances to the Connect Endoscope state 278 and prompts the user to install the endoscope in the cannula. In some embodiments, a voice prompts the user to perform this task, since their attention is on the arms and not the screen. In one example, the system speaks, "Now install the endoscope". The system is arranged to sense when the endoscope is installed without the user manually inputting a setting. When the endoscope is detected as being installed, the guided setup advances to the Targeting state 280, and the touchscreen monitor 146 prompts the user to perform targeting at 342. Some embodiments of the system use a voice prompt here that says, for example, "Point the scope at the target anatomy, then press and hold the targeting button". This may include pointing the endoscope at the target anatomy and pressing and holding a targeting button. In some embodiments, the targeting button is disposed on the endoscope instrument. However, it may be disposed at other locations about the device. In some embodiments, the target button is disposed on the spar 172 of the arm 106.

When the targeting button is held in its operate position, the system rotates the orienting platform so that a centerline of the orienting platform 107 is oriented with the endoscope. Here, the camera arm (the arm connected to the endoscope) moves as the orienting platform 107 moves so that the endoscope stays at its position and orientation with reference to the patient. This camera arm motion is null space motion to counteract the orienting platform 107 motion. In addition, the boom 105 and the other arms 106 are positioned based on the camera arm's position to refine the ideal spot for the arms with reference to the endoscope position and orientation, as well as to the positions of the other arms. For example, the non-sterile height of the orienting platform 107 is set to not be too low, which might cause contact with a sterile instrument during insertion or removal, but not too high at an opposite end of its range of motion. The boom 105 and the orienting platform 107 will move so that the crosshair is laterally aligned with the remote center of motion for the camera manipulator. If during targeting, the boom 105 is moved too far out, near the boom's outer range of motion, the visual and audio warning are output that advise the user to move the teleoperational assembly 100 closer to the patient.

At a step 344, the central electronic data processing unit 142 may query whether a user docked a second cannula before performing the targeting. If this occurred before targeting, the touchscreen monitor 146 displays a targeting reminder prompt on the touchscreen monitor 146 at 346. If the user performs targeting as prompted at 342, and does not add a second cannula before targeting, then the touchscreen monitor 146 advances to the Connect Remaining Arms state 282 and prompts the user to dock cannulas to the rest of the arms at 348. When the rest of the arms are docked, the guided setup advances to the Surgery In Process state 284, and the guided setup process ends at 350. Information relating to the surgery may then be displayed on the touchscreen monitor 146.

The guided setup system allows a user to deviate from the given sequence in a manner that provides a dynamic setup and that provides many options to a user. In addition to advancing through the setup without requiring the user to indicate when a step is complete, the guided setup also includes a plurality of universal overrides that cause the guided setup to skip or bypass particular states. These overrides occur when a user performs an action that causes the system to change states without following the sequence set out above.

One exemplary universal override occurs when a user docks an arm to a cannula. In this condition, regardless of the operating state of the guided setup, whether at the Deploy For Draping state, the Select Anatomy state, or any other state, the touchpad 154 advances to the Surgery In Process state 276 and displays the surgery in process prompt. In addition, the touchscreen monitor 146 advances to the Dock Scope Arm state. Accordingly, if, for example, the system is setup for a training exercise or for instruction, docking a cannula resets the touchpad 154 to the Surgery In Process state and resets the touchscreen monitor to the Dock Scope Arm state regardless of their current states.

The guided setup system includes additional universal overrides that cause the system to skip over some states to a preset state associated with the override. For example, irrespective of the current state, if a user attaches a valid instrument to a cannula docked on an arm, the touchscreen monitor 146 advances to the Surgery In Process state 284, and the touchscreen monitor 146 displays the surgery in process prompt. This ends the guided walkthrough until all cannulae are again removed. In another example, irrespective of the current state, if an arm is properly draped, and the arm is docked to cannula, and an endoscope is not attached, then the touchscreen monitor 146 displays a prompt to connect an endoscope to the arm.

Yet another universal override condition occurs when an endoscope is properly connected, the system is not targeted, and the arms are enabled. In this override condition, the guided setup system advances to the Targeting state 280 and prompts the user to target by instructing the user to point at the target anatomy and press and hold the targeting button.

It is worth noting that the guided setup system is configured to automatically recognize when a state is met, and the system automatically advances to the next state. Accordingly, the user need not enter a "next" input at any time. Furthermore, a user can override/skip one or more parts of the guided setup system by simply moving directly to a system configuration farther along in the guided setup process, at which point the system will sense the configuration and output an appropriate prompt corresponding to the configuration. That is, the context of the configuration determines what the system infers is the next required action. If the system determines that a user appears to have skipped an action that has been identified in the system as being especially important, the system will output a reminder. But if the user continues after receiving the reminder, the system continues and outputs the next prompt based on the sensed configuration. In this manner, the system guides the setup without requiring a particular sequence of action and without requiring that all steps be taken into account. Accordingly, skilled or practiced users may be able to setup the system without precisely following the guided setup prompts, while other users may wish to precisely follow the guided setup prompts. Furthermore, because the user need not enter a "next" input after any step, the setup process may be completed in less time, may result in less contamination, and may enable simple setup for training, practice, or instructional purposes, without requiring the system to go through a complete surgical preparation.

Although illustrative embodiments have been shown and described, a wide range of modification, change and substitution is contemplated in the foregoing disclosure and in some instances, some features of the embodiments may be employed without a corresponding use of other features. One of ordinary skill in the art would recognize many variations, alternatives, and modifications. Thus, the scope of the disclosure should be limited only by the following claims, and it is appropriate that the claims be construed broadly and in a manner consistent with the scope of the embodiments disclosed herein.

What is claimed is:

1. A teleoperational medical system for performing a medical procedure, the system comprising:
   a teleoperational assembly including a motorized setup structure and a plurality of motorized arms configured to assist in the medical procedure;
   a memory storing a plurality of pre-established positions associated with different phases of the medical procedure;
   an input device configured to receive an input to move all arms of the plurality of motorized arms to a selected pre-established position of the plurality of pre-established positions; and
   a processing system configured to:
      receive the input from the input device; and
      output control signals to the setup structure and to each arm of the plurality of motorized arms to move each arm of the plurality of motorized arms to the selected pre-established position.

2. The teleoperational medical system of claim 1, wherein the input device is configured to receive an input identifying a portion of a patient's anatomy to be treated in the medical procedure, the selected pre-established position of the plurality of pre-established positions being based on the input identifying a portion of the patient's anatomy.

3. The teleoperational medical system of claim 1, wherein the input device is configured to receive an input identifying an approach to a patient to be treated in the medical procedure, the selected pre-established position of the plurality of pre-established positions being based on the input identifying the approach to the patient.

4. The teleoperational medical system of claim 3, wherein the approach to the patient to be treated is one of a left side approach, a right side approach, and a leg approach.

5. The teleoperational medical system of claim 1, wherein the selected pre-established position is a docking position, and wherein in the docking position each arm of the plurality of motorized arms is deployed in a position for advancing over a patient.

6. The teleoperational medical system of claim 5, wherein the teleoperational assembly comprises a boom and a rotatable platform rotatably connected to the boom, the plurality of motorized arms extending from the rotatable platform, and wherein the processing system is configured to rotate the rotatable platform relative to the boom in response to the input received at the input device.

7. The teleoperational medical system of claim 5, wherein each arm of the plurality of motorized arms has a corresponding total range of motion, and wherein the selected pre-established position places each arm of the plurality of motorized arms within a range of 30-70% of the corresponding total range of motion.

8. The teleoperational medical system of claim 5, wherein the teleoperational assembly comprises a telescoping column and a telescoping boom extending from the column, the plurality of motorized arms being carried on the boom, wherein the boom has a total range of motion, and wherein the selected pre-established position for the boom is within a range of 30-70% of the total range of motion.

9. The teleoperational medical system of claim 1, wherein the selected pre-established position is a draping position, wherein in the draping position each arm of the plurality of motorized arms is deployed in a position suitable for receiving a drape.

10. The teleoperational medical system of claim 9, wherein the teleoperational assembly comprises:
a column with an adjustable height; and
a boom extending from the column, the boom having an adjustable length, the plurality of motorized arms being carried on the boom,
wherein the draping position comprises a partially raised column and a partially extended boom.

11. The teleoperational medical system of claim 1, wherein the selected pre-established position is a stow position wherein each arm of the plurality of motorized arms is deployed in a fully retracted position to minimize an overall footprint of the teleoperational assembly.

12. The teleoperational medical system of claim 11, wherein the teleoperational assembly comprises:
a column with an adjustable height; and
a boom extending from the column, the boom having an adjustable length, the plurality of motorized arms being carried on the boom,
wherein the stowed position comprises a fully retracted column and fully retracted arms.

13. The teleoperational medical system of claim 1, wherein a pre-established position of the plurality of pre-established positions is based on a patient dimension.

14. A method of controlling a teleoperational medical system, the method comprising:
receiving an input at a user interface to move all arms of a plurality of motorized arms of a teleoperational assembly to a position of a plurality of pre-established positions, the plurality of pre-established positions being associated with different phases of a medical procedure; and
outputting a control signal to each arm of the plurality of motorized arms to move each arm of the plurality of motorized arms to the position of the plurality of pre-established positions.

15. The method claim 14, further comprising receiving an input identifying a portion of a patient's anatomy to be treated in the medical procedure, wherein the control signal to each arm is based on the input identifying the portion of the patient's anatomy.

16. The method of claim 14, further comprising receiving an input identifying an approach to a patient to be treated in the medical procedure, wherein the control signal to each arm is based on the input identifying the approach to the patient.

17. The method of claim 16, wherein receiving an input identifying an approach comprises receiving an input identifying one of a left side approach, a right side approach, and a leg approach.

18. The method of claim 14, wherein outputting a control signal to each arm of the plurality of motorized arms comprises outputting a control signal to raise each arm of the plurality of motorized arms to a position for advancing over a patient.

19. The method of claim 18, wherein the teleoperational assembly comprises a boom and a rotatable platform portion rotatably connected to the boom, the motorized arms extending from the rotatable platform portion, the method further comprising outputting a control signal to the rotatable platform portion to rotate the platform portion relative to the boom in response to the input received at the user interface.

20. The method of claim 18, wherein each arm of the plurality of motorized arms has a corresponding total range of motion, and wherein the pre-established position for each arm of the plurality of motorized arms is within a range of 30-70% of the corresponding total range of motion.

21. A method of controlling a teleoperational medical system, the method comprising:
receiving an anatomical input identifying a portion of a patient's anatomy to be treated in a medical procedure;
receiving an approach input identifying an approach to the patient to be treated in the medical procedure; and
outputting a control signal to each arm of a plurality of motorized arms of a teleoperational assembly to move each arm of the plurality of motorized arms to a pre-established position of a plurality of pre-stored pre-established positions based on both the anatomical input identifying the portion of the patient's anatomy and the approach input identifying the approach to the patient.

22. The method of claim 21, comprising receiving an actuating input at a user interface to move all arms of the plurality of motorized arms of the teleoperational assembly to the pre-established position, wherein outputting the control signal to each arm of the plurality of motorized arms is in response to the received actuating input.

23. The method of claim 22, wherein outputting the control signal to each arm of the plurality of motorized arms occurs only while the actuating input is being received.

* * * * *